(12) United States Patent
Higuchi et al.

(10) Patent No.: US 11,203,755 B2
(45) Date of Patent: Dec. 21, 2021

(54) CHEMICALLY-MODIFIED SIRNA

(71) Applicant: NapaJen Pharma, Inc., Burlingame, CA (US)

(72) Inventors: Sadaharu Higuchi, Koganei (JP); Atsushi Uno, Koganei (JP); Hironori Ando, Koganei (JP)

(73) Assignee: NapaJen Pharma, Inc., Burlingame, CA (US)

( * ) Notice: Subject to any disclaimer, the term of this patent is extended or adjusted under 35 U.S.C. 154(b) by 0 days.

(21) Appl. No.: 16/463,666

(22) PCT Filed: Nov. 27, 2017

(86) PCT No.: PCT/JP2017/042439
§ 371 (c)(1),
(2) Date: May 23, 2019

(87) PCT Pub. No.: WO2018/097296
PCT Pub. Date: May 31, 2018

(65) Prior Publication Data
US 2019/0382762 A1     Dec. 19, 2019

(30) Foreign Application Priority Data
Nov. 28, 2016   (JP) .............................. JP2016-230640

(51) Int. Cl.
*C12N 15/113*          (2010.01)
(52) U.S. Cl.
CPC ........ *C12N 15/113* (2013.01); *C12N 2310/14* (2013.01); *C12N 2310/315* (2013.01); *C12N 2310/351* (2013.01); *C12N 2320/51* (2013.01)

(58) Field of Classification Search
None
See application file for complete search history.

(56) References Cited

U.S. PATENT DOCUMENTS

| 2005/0282188 | A1* | 12/2005 | Haeberli | ............... | C07H 21/02 435/6.11 |
| 2011/0111501 | A1 | 5/2011 | Kubo et al. | | |
| 2013/0142832 | A1 | 6/2013 | Sakurai et al. | | |
| 2014/0128448 | A1 | 5/2014 | Rii et al. | | |
| 2014/0294869 | A1 | 10/2014 | Rii et al. | | |
| 2016/0304883 | A1 | 10/2016 | Grund et al. | | |
| 2017/0175128 | A1 | 6/2017 | Welstead et al. | | |
| 2017/0202979 | A1 | 7/2017 | Chakraborty et al. | | |

FOREIGN PATENT DOCUMENTS

| EP | 2 226 384 A1 | 9/2010 |
| EP | 2 865 759 A1 | 4/2015 |
| OA | WO 2012/117855 A1 | 9/2012 |
| RU | 2489167 | 11/2011 |
| WO | WO 2005/089224 A2 | 9/2005 |
| WO | WO 2005/115481 A2 | 12/2005 |
| WO | WO 2009/078470 A1 | 6/2009 |
| WO | WO 2012/020795 A1 | 2/2012 |
| WO | WO 2013/021784 A1 | 2/2013 |
| WO | WO 2015/101415 A1 | 7/2015 |
| WO | WO 2015/161276 A1 | 10/2015 |
| WO | WO 2016/011306 A2 | 1/2016 |
| WO | WO 2016/161374 A1 | 10/2016 |

OTHER PUBLICATIONS

Allerson et al (J. Med. Chem. 2005, 48, 901-904) (Year: 2005).*
International Search Report dated Feb. 20, 2018 in PCT/JP2017/042439 filed Nov. 27, 2017.
Bramsen, J. B. et al., "Development of therapeutic-grade small interfering RNAs by chemical engineering," Frontiers in Genetics, vol. 3, No. 154, Aug. 20, 2012, pp. 1-22.
Lundin, K. E. et al., "Oligonucleotide Therapies: The Past and the Present," Human Gene Therapy, vol. 26, No. 8, Aug. 1, 2015, pp. 475-485.
Dar, S. A. et al., "siRNAmod: A database of experimentally validated chemically modified siRNAs," Scientific Reports, vol. 6, No. 20031, Jan. 28, 2016, pp. 1-8.
Ozcan, G. et al., "Preclinical and clincial development of siRNA-based therapeutics," Adv Drug Deliv Rev., vol. 87, Jun. 29, 2015, published in final edited form as pp. 108-119 (26 pages).
Extended European Search Report dated May 29, 2020, in Patent Application No. 17872923.2, 6 pages.
Office Action as received in the counterpart Russian Patent Application No. 2019119833 dated Apr. 2, 2021, 7 pages.

* cited by examiner

*Primary Examiner* — Richard A Schnizer
(74) *Attorney, Agent, or Firm* — Oblon, McClelland, Maier & Neustadt, L.L.P.

(57) ABSTRACT

An objective of the present invention is to provide a chemically-modified siRNA that has polydeoxyadenylic acid added to the 5' end of the sense strand, and, when complexed with schizophyllan, is high in resistance against RNase and moreover effectively exhibits RNAi activity. To achieve the objective, in the chemically-modified siRNA with polydeoxyadenylic acid added to the 5' end of the sense strand, specific chemical modification is performed for dinucleotide sequences of CA, UA, and UG in the base sequence of the sense strand and dinucleotide sequences of CA, UA, and UG in the base sequence at and after the eighth base from the 5' end of the antisense strand.

24 Claims, 5 Drawing Sheets

Specification includes a Sequence Listing.

1. Naked 20ng
2. Complex 200ng

<1min>
3. NJO50.14 complex 200ng in mouse Serum 400ng
4. NJO50.14 complex 200ng in human serum 400ng
5. NJO50.14 complex 200ng in fetal bovine serum 400ng 6. Mouse serum
7. Human serum
8. Fetal bovine serum <30min>
9. NJO50.14 complex 200ng in mouse Serum 400ng
10. NJO50.14 complex 200ng in human serum 400ng
11. NJO50.14 complex 200ng in fetal bovine serum 400ng 12. 21mer

CHEMICALLY-MODIFIED SIRNA

TECHNICAL FIELD

The present invention relates to a chemically-modified siRNA, and more particularly to a chemically-modified siRNA that has polydeoxyadenylic acid added to the 5' end of the sense strand, and, when complexed with schizophyllan, is high in resistance against RNase and moreover effectively exhibits RNAi activity.

BACKGROUND ART

RNA interference (RNAi) discovered in 1998 is an epoch-making gene expression inhibition method, with the magnitude and persistence of its effect being significantly superior to the conventional antisense method, and therefore medicinal use of RNAi has been expected. However, since a double-stranded RNA exhibiting RNAi activity (i.e., siRNA) is often degraded in the course from administration to uptake into a target cell or inside the cell, it has been difficult to form a RISC complex as its active body inside the cell.

Unmodified siRNAs designed according to a suitable algorithm are degraded quite easily with RNase present in a blood, for example, due to in-vivo and intracellular fragility for achievement of expected RNAi activity, resulting in that only a few of such siRNAs exert RNAi effect in a target cell. Conventionally, therefore, it has been proposed to chemically modify siRNAs in various ways to impart RNase resistance (Non-Patent Documents 1 to 3). However, in most of siRNAs developed as nucleic acid medicine, all bases have been chemically modified, and this causes the results of failing to achieve the RNAi activity expected for unmodified siRNAs at the initial sequence design. That is, presently, there has not been found such a chemically-modified siRNA that is excellent in RNase resistance with small chemical modification and induces RNAi activity as originally expected (Non-Patent Document 4).

Meanwhile, as an siRNA delivery technology, there has been proposed an siRNA/SPG complex of an siRNA with polydeoxyadenylic acid added thereto and schizophyllan (SPG) (see Patent Document 1). The siRNA/SPG complex can selectively deliver the siRNA to a Dectin-1 expression cell such as a dendritic cell, and moreover, once the siRNA is delivered to a cell, it can effectively exert the RNAi effect. Therefore, commercialization of this complex as nucleic acid medicines is expected. Since the siRNA/SPG complex is in the state in which the siRNA is embedded in SPG, some degree of RNase resistance is expected, but degradation with RNase is unavoidable inside a blood where a large amount of RNase is present. In order to develop the siRNA/SPG complex as nucleic acid medicines, therefore, it is desired to develop a technology of improving the resistance against RNase while maintaining the RNAi activity.

PRIOR ART DOCUMENTS

Non-Patent Documents

Non-Patent Document 1: Development of Therapeutic-Grade Small Interfering RNAs by Chemical Engineering, Jesper B. Bramsen and Jorgen Kjems, Front Genet. 2012; 3: 54

Non-Patent Document 2: Oligonucleotide Therapies: The past and the Present, Karin E. Lundin, Olof Gissberg, and C. I. Edvard Smith, Hum Gene Ther. 2015 Aug. 1; 26(8): 475-485

Non-Patent Document 3: siRNAmod: A database of experimentally validated chemically modified siRNAs, Showkat Ahmad Dar, Anamika Thakur, Abid Qureshi & Manoj Kumar, Sci Rep. 2016; 6: 20031

Non-Patent Document 4: Preclinical and clinical development of siRNA-based therapeutics, Gulnihal Ozcan, Bulent Ozpolat, Robert L. Coleman, Anil K. Sood, and Gabriel Lopez-Berestein, Adv Drug Deliv Rev. 2015 Jun. 29; 87: 108-119

PATENT DOCUMENT

Patent Document 1: WO2009/078470

SUMMARY OF THE INVENTION

Problems to be Solved by the Invention

An objective of the present invention is to provide a chemically-modified siRNA that has polydeoxyadenylic acid (used to mean to also include phosphorothioated polydeoxyadenylic acid unless otherwise specified) added to the 5' end of the sense strand, and, when complexed with schizophyllan, is high in resistance against RNase and moreover effectively exhibits RNAi activity.

Means for Solving the Problem

For improving the resistance against RNase by chemically modifying the siRNA that has polydeoxyadenylic acid added to the 5' end of the sense strand, those skilled in the art will normally consider it essential to strengthen the resistance against RNase by chemical modification at the following two locations: (1) the 5' end side of the antisense strand that is considered especially weak in binding force with the sense strand and (2) the neighborhood of the connection point between the siRNA and polydeoxyadenylic acid. However, the present inventors have confirmed that the chemical modification at these two locations would not sufficiently improve the resistance against RNase. The inventors have further examined chemical modification methods for siRNAs reported in known documents.

Under the above-described circumstances, the present inventors have performed keen examination and found the followings. By imparting specific chemical modification to a specific base, for the siRNA that has polydeoxyadenylic acid added to the 5' end of the sense strand, compared to a normal siRNA with no polydeoxyadenylic acid added thereto, it is possible to markedly improve the resistance against RNase for the siRNA that has polydeoxyadenylic acid added to the 5' end of the sense strand when complexed with schizophyllan, even with comparatively small chemical modification, and effectively exhibit RNAi activity. The present invention has been accomplished by piling examination upon examination based on the above findings.

That is, the present invention is presented in the following forms. Note herein that the modification method according to the present invention represented by conditions (i) to (ix) in item 1 below is also referred to as A-3 modification.

Item 1. A chemically-modified siRNA with polydeoxyadenylic acid added to 5' end of a sense strand, wherein a base sequence of the sense strand includes at least one kind of dinucleotide sequence selected from the group consisting of CA, UA, and UG, and a base sequence at and after the eighth base from a 5' end of an anti sense strand includes at least one kind of dinucleotide sequence selected from the group consisting of CA, UA, and UG, and conditions (i) to (ix) below are satisfied:

(i) when the dinucleotide sequence constituted by CA is included in the base sequence of the sense strand, a fluoro group has substituted for a hydroxy group at 2' position of a cytidylic acid residue in the dinucleotide sequence, and a methoxy group has substituted for a hydroxy group at 2' position of an adenylic acid residue in the dinucleotide sequence;

(ii) when the dinucleotide sequence constituted by UA is included in the base sequence of the sense strand, a fluoro group has substituted for a hydroxy group at 2' position of a uridylic acid residue in the dinucleotide sequence, and a methoxy group has substituted for a hydroxy group at 2' position of an adenylic acid residue in the dinucleotide sequence;

(iii) when the dinucleotide sequence constituted by UG is included in the base sequence of the sense strand, a fluoro group has substituted for a hydroxy group at 2' position of a uridylic acid residue in the dinucleotide sequence, and a methoxy group has substituted for a hydroxy group at 2' position of a guanylic acid residue in the dinucleotide sequence;

(iv) when the dinucleotide sequence constituted by CA is included in the base sequence at and after the eighth base from the 5' end of the antisense strand, a fluoro group has substituted for a hydroxy group at 2' position of a cytidylic acid residue in the dinucleotide sequence, and a methoxy group has substituted for a hydroxy group at 2' position of an adenylic acid residue in the dinucleotide sequence;

(v) when the dinucleotide sequence constituted by UA is included in the base sequence at and after the eighth base from the 5' end of the antisense strand, a fluoro group has substituted for a hydroxy group at 2' position of a uridylic acid residue in the dinucleotide sequence, and a methoxy group has substituted for a hydroxy group at 2' position of an adenylic acid residue in the dinucleotide sequence;

(vi) when the dinucleotide sequence constituted by UG is included in the base sequence at and after the eighth base from the 5' end of the antisense strand, a fluoro group has substituted for a hydroxy group at 2' position of a uridylic acid residue in the dinucleotide sequence, and a methoxy group has substituted for a hydroxy group at 2' position of a guanylic acid residue in the dinucleotide sequence;

(vii) the first to seventh ribonucleotide residues from the 5' end of the antisense strand have not undergone chemical modification;

(viii) when neither the first ribonucleotide residue from the 5' end of the sense strand nor the nineteenth ribonucleotide residue from the 5' end of the antisense strand is chemically modified in the chemical modification according to the conditions (i) to (vi), if the first ribonucleotide residue from the 5' end of the sense strand is a cytidylic acid residue or a uridylic acid residue, a hydroxy group at 2' position has been modified by a fluoro group, and if the ribonucleotide residue is an adenylic acid residue or a guanylic acid residue, a hydroxy group at 2' position has been modified by a methoxy group; and (ix) when both the first ribonucleotide residue from the 5' end of the sense strand and the nineteenth ribonucleotide residue from the 5' end of the antisense strand are chemically modified in the chemical modification according to the conditions (i) to (vi), the nineteenth ribonucleotide residue from the 5' end of the antisense strand have not undergone chemical modification.

Item 2. The chemically-modified siRNA according to item 1, wherein the polydeoxyadenylic acid has a base length of 10 to 100.

Item 3. A schizophyllan/chemically-modified siRNA complex, wherein the chemically-modified siRNA according to item 1 or 2 is complexed with schizophyllan.

Advantages of the Invention

According to the present invention, it is possible to present a chemically-modified siRNA that has polydeoxyadenylic acid added to the 5' end of the sense strand, obtained by imparting comparatively small chemical modification, and is high in resistance against RNase and moreover effectively exhibits RNAi activity when complexed with schizophyllan.

EMBODIMENTS OF THE INVENTION

Figure 1:
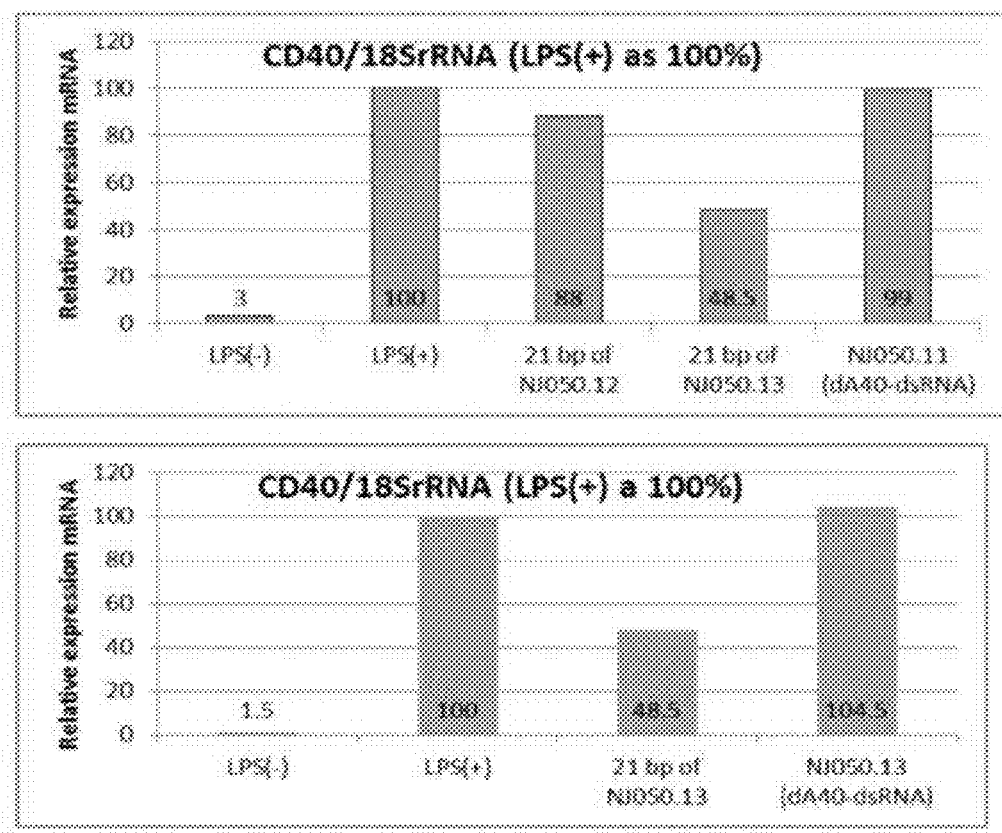
FIG. 1 shows the results of evaluation of the gene expression inhibition effect for various chemically-modified siRNAs and SPG/chemically-modified siRNA complexes using chemically-modified siRNAs in Reference Test Example 1.

In the present invention, in a base sequence constituted by two or more bases, the left end of the base sequence is referred to as the 5' end and the right end as the 3' end.

1. Chemically-Modified siRNA

Base Sequence/Structure of siRNA with Polydeoxyadenylic Acid Added Thereto

A chemically-modified siRNA of the present invention has the following features: polydeoxyadenylic acid is added to the 5' end of the sense strand, the sense strand and the antisense strand include a specific dinucleotide sequence, and the dinucleotide sequence has undergone specific chemical modification. Hereinafter, the chemically-modified siRNA of the present invention will be described in detail.

In the chemically-modified siRNA of the present invention, the base sequences of the sense strand and the antisense strand are set depending on a target sequence in a target gene. The target sequence in the target gene can be set by a known technique according to the manual of Integrated DNA Technologies, Inc. (IDT) (Dicer Substrate RNAi Design), etc. Normally, an siRNA is designed to include a sequence 100% identical to the target sequence or a sequence in which substitution/addition of one or several bases has been made from the target sequence as long as a desired RNA interference effect can be obtained. Also, it is reported that an siRNA having an excellent RNA interference effect can be designed by designing a double-stranded RNA in which the 5' end of the antisense strand is an A/U pair, the 5' end of the sense strand is a G/C pair, approximately five A/U pairs are present on the 5' end side of the antisense strand, and nine or more G/C pairs are not present in the double strands (Ui-Tei et al, Nucleic Acids Res., 32, 936-948 (2004)). For example, as siRNAs for CD40, listed are: an siRNA having a sense strand made of a base sequence represented by SEQ ID NO: 1 and an antisense strand made of a base sequence represented by SEQ ID NO: 2; an siRNA having a sense strand made of a base sequence represented by SEQ ID NO: 3 and an antisense strand made of a base sequence represented by SEQ ID NO: 4; an siRNA having a sense strand made of a base sequence represented by SEQ ID NO: 5 and an antisense strand made of a base sequence represented by SEQ ID NO: 6; an siRNA having a sense strand made of a base sequence represented by SEQ ID NO: 7 and an antisense strand made of a base sequence represented by SEQ ID NO: 8, and an siRNA having a sense strand made of a base sequence represented by SEQ ID NO: 9 and an antisense strand made of a base sequence represented by SEQ ID NO: 10.

In the chemically-modified siRNA of the present invention, the base sequence of the sense strand includes at least one kind of dinucleotide sequence selected from the group consisting of CA, UA, and UG, and the base sequence at and after the eighth base from the 5' end of the antisense strand includes at least one kind of dinucleotide sequence selected from the group consisting of CA, UA, and UG. By imparting specific chemical modification to be described later to such dinucleotide sequences, it is possible to improve the resistance against RNase while maintaining RNAi activity when the siRNA is complexed with SPG.

The target gene for the chemically-modified siRNA of the present invention is not specifically restricted, but may be appropriately selected based on the use of the chemically-modified siRNA. From the standpoint of medicinal use, however, a gene that is related to a clinical condition and of which expression inhibition is desired is preferred.

As a preferred form of a target gene for the chemically-modified siRNA of the present invention, there is a gene that is expressed in a Dectin-1 expression cell and affects an in-vivo function by the cell. Dectin-1 is a receptor having a C-type leptin type sugar chain recognition domain (pattern recognition receptor) present on a cell membrane. Dectin-1 has a region specifically recognizing SPG outside the cell and has a motif transmitting an activation signal called immunoreceptor tyrosinase-based activation motif-1 (ITAM) inside the cell. Once recognizing SPG, Dectin-1 urges production of NF-κB and inflammatory cytokine, giving rise to biological defense reaction. Concrete examples of Dectin-1 expression cells include macrophages, dendritic cells, and neutrophils. SPG has a β-1,3-glucan structure, and is known to bind to Dectin-1 present on the cell membrane of the Dectin-1 expression cell, thereby being delivered into the Dectin-1 expression cell by endocytosis. When the chemically-modified siRNA of the present invention is complexed with SPG, SPG is recognized by Dectin-1, whereby the chemically-modified siRNA of the present invention can be selectively delivered into the Dectin-1 expression cell. Also, by selecting a gene that affects an in-vivo function born by the Dectin-1 expression cell as the target gene for the chemically-modified siRNA of the present invention, in-vivo immunosuppression is induced, making it possible to regulate the immunity.

In the chemically-modified siRNA of the present invention, when a gene that is expressed in the Dectin-1 expression cell and affects an in-vivo function born by the cell is used as the target gene, the kind of the gene is not specifically restricted, but can be appropriately selected based on the use of the chemically-modified siRNA of the present invention. From the standpoint of inducing the in-vivo immune modulation, especially immunosuppression, more effectively, however, genes related to antigen presentation including a gene coding a costimulatory factor (also called a costimulatory molecule) such as CD40 are listed as preferred target genes.

In the chemically-modified siRNA of the present invention, the base lengths of the sense strand and the antisense strand are not specifically restricted, but preferably 21.

Also, in the chemically-modified siRNA of the present invention, the sense strand and the antisense strand each may be hybridized to have a dangling end made of approximately two to five ribonucleotides or deoxyribonucleotides at the 3' end, to form the double strands.

As an example of a preferred form of the chemically-modified siRNA of the present invention, presented is one in which the base lengths of the sense strand and the antisense strand are both 21, and a dangling end made of two ribonucleotides or deoxyribonucleotides is formed each at the 5' end of the sense strand and the 3' end of the antisense strand. That is, in such an siRNA, the sequence of the third to twenty-first ribonucleotides from the 3' end of the antisense strand is complementary to the sequence of the first to nineteenth ribonucleotides from the 5' end of the sense strand.

In the chemically-modified siRNA of the present invention, polydeoxyadenylic acid is added to the 5' end of the sense strand. The polydeoxyadenylic acid forms a triple helical structure with two units of SPG, playing a role of complexing the chemically-modified siRNA of the present invention with SPG.

The number of deoxyadenylic acid residues constituting the polydeoxyadenylic acid is not specifically restricted as long as formation of a complex with SPG is possible, but may be 10 to 100, for example, preferably 20 to 100, more preferably 20 to 80, further preferably 30 to 50.

In the chemically-modified siRNA of the present invention, the polydeoxyadenylic acid is preferably directly bonded to the 5' end of the sense strand by phosphodiester bonding, but may be bonded to the 5' end of the sense strand via a linker (spacer).

Also, in the chemically-modified siRNA of the present invention, the phosphodiester bonds of the sense strand, antisense strand, and the polydeoxyadenylic acid may be partly or entirely phosphorothioated (sulfurized). The polydeoxyadenylic acid moiety of the chemically-modified siRNA of the present invention is preferably sulfurized. The sulfurized phosphodiester bond refers to a bond structure in which a sulfur atom has substituted for one of oxygen atoms of the phosphate residue in the phosphodiester bond moiety.

Chemical Modification of siRNA

The chemically-modified siRNA of the present invention has undergone chemical modification according to conditions (i) to (ix) to be described later (A-3 modification) in its sense strand and antisense strand. Note that, in the chemically-modified siRNA of the present invention, it is necessary not to perform any chemical modification other than the conditions (i) to (ix) to be described later for the sense strand and the antisense strand.

<Chemical Modification of Sense Strand>

The sense strand of the chemically-modified siRNA of the present invention undergoes chemical modification so as to satisfy the following conditions (i) to (iii).

(i) When a dinucleotide sequence constituted by CA is included in the base sequence of the sense strand, a fluoro group has substituted for the hydroxy group at the 2' position of the cytidylic acid residue in the dinucleotide sequence, and a methoxy group has substituted for the hydroxy group at the 2' position of the adenylic acid residue in the dinucleotide sequence.

(ii) When a dinucleotide sequence constituted by UA is included in the base sequence of the sense strand, a fluoro group has substituted for the hydroxy group at the 2' position of the uridylic acid residue in the dinucleotide sequence, and a methoxy group has substituted for the hydroxy group at the 2' position of the adenylic acid residue in the dinucleotide sequence.

(iii) When a dinucleotide sequence constituted by UG is included in the base sequence of the sense strand, a fluoro group has substituted for the hydroxy group at the 2' position of the uridylic acid residue in the dinucleotide sequence, and a methoxy group has substituted for the hydroxy group at the 2' position of the guanylic acid residue in the dinucleotide sequence.

That is, when the sense strand of the siRNA has a base sequence having a base length of 21 shown in (A) of Table 1, for example, the form shown in (B) of Table 1 is exemplified as the one that has undergone the chemical modification according to the conditions (i) to (iii).

TABLE 1

| | |
|---|---|
| (A) Sense strand before chemical modification | 5'-CGUGCAGUGACAAACAGUAdtdt-3' (SEQ ID NO: 11) ↓ |
| (B) Sense strand after chemical modification according to conditions (i) to (iii) | 5'-CGU(F)G(M)C(F)A(M)GU(F)G(M)AC(F)A(M)AAC(F)A(M)GU(F)A(M)dtdt-3' (SEQ ID NO: 12) |

In Table, "dt" denotes a deoxythymidylic acid residue, "U(F)" a uridylic acid residue where the hydroxy group at 2' position has been modified with a fluoro group, "G(M)" a guanylic acid residue where a methoxy group has substituted for the hydroxy group at 2' position, "C(F)" a cytidylic acid residue where the hydroxy group at 2' position has been modified with a fluoro group, and "A(M)" an adenylic acid residue where a methoxy group has substituted for the hydroxy group at 2' position.

In Table, "dt" denotes a deoxythymidylic acid residue, "U(F)" a uridylic acid residue where the hydroxy group at 2' position has been modified with a fluoro group, "G(M)" a guanylic acid residue where a methoxy group has substituted for the hydroxy group at 2' position, "C(F)" a cytidylic acid residue where the hydroxy group at 2' position has been modified with a fluoro group, and "A(M)" an adenylic acid residue where a methoxy group has substituted for the hydroxy group at 2' position.

<Chemical Modification of Antisense Strand>

The antisense strand of the chemically-modified siRNA of the present invention undergoes chemical modification so as to satisfy the following conditions (iv) to (vii).

(iv) When a dinucleotide sequence constituted by CA is included in the base sequence at and after the eighth base from the 5' end of the antisense strand, a fluoro group has substituted for the hydroxy group at the 2' position of the cytidylic acid residue in the dinucleotide sequence, and a methoxy group has substituted for the hydroxy group at the 2' position of the adenylic acid residue in the dinucleotide sequence.

(v) When a dinucleotide sequence constituted by UA is included in the base sequence at and after the eighth base from the 5' end of the antisense strand, a fluoro group has substituted for the hydroxy group at the 2' position of the uridylic acid residue in the dinucleotide sequence, and a methoxy group has substituted for the hydroxy group at the 2' position of the adenylic acid residue in the dinucleotide sequence.

(vi) When a dinucleotide sequence constituted by UG is included in the base sequence at and after the eighth base from the 5' end of the antisense strand, a fluoro group has substituted for the hydroxy group at the 2' position of the uridylic acid residue in the dinucleotide sequence, and a methoxy group has substituted for the hydroxy group at the 2' position of the guanylic acid residue in the dinucleotide sequence.

(vii) The first to seventh ribonucleotide residues from the 5' end of the antisense strand have not undergone chemical modification.

That is, when the antisense strand of the siRNA has a base sequence having a base length of 21 shown in (A) of Table 2, for example, the form shown in (B) of Table 2 is exemplified as the one that has undergone the chemical modification according to the conditions (iv) to (vii).

TABLE 2

| | |
|---|---|
| (A) Sense strand before chemical modification | 5'-UACUGUUUGUCACUGCACGdtdt-3' (SEQ ID NO: 13) |
| | ↓ |
| (B) Sense strand after chemical modification according to conditions (iv) to (vii) | 5'-UACUGUUU(F)G(M)UC(F)A(M)CU(F)G(M)C(F)A(M)CGdtdt-3' (SEQ ID NO: 14) |

In Table, "dt", "U(F)", "G(M)", and "A(M)" are as defined in Table 1.

In Table, "dt", "U(F)", "G(M)", and "A(M)" are as defined in Table 1.

<Chemical Modification in the Neighborhood of Polydeoxyadenylic Acid>

In the chemically-modified siRNA of the present invention, the first ribonucleotide residue from the 5' end of the sense strand and the nineteenth ribonucleotide residue from the 5' end of the antisense strand are located at positions closest to the polydeoxyadenylic acid. In the chemically-modified siRNA of the present invention, the above conditions (i) to (vii) should not be applied to these ribonucleotide residues as they are in some cases.

Concretely, in the chemically-modified siRNA of the present invention, the sense strand and the antisense strand undergo the chemical modification according to the above conditions (i) to (vii). However, in the case that neither the first ribonucleotide residue from the 5' end of the sense strand nor the nineteenth ribonucleotide residue from the 5' end of the antisense strand is chemically modified, or both of them are chemically modified, in the chemical modification according to these conditions, chemical modification according to conditions (viii) and (ix) below is necessary.

(viii) When neither the first ribonucleotide residue from the 5' end of the sense strand nor the nineteenth ribonucleotide residue from the 5' end of the antisense strand is chemically modified in the chemical modification according to the conditions (i) to (vi), if the first ribonucleotide residue from the 5' end of the sense strand is a cytidylic acid residue or a uridylic acid residue, the 2' position thereof has been modified with a fluoro group, and if the ribonucleotide residue is an adenylic acid residue or a guanylic acid residue, the 2' position thereof has been modified with a methoxy group.

(ix) When both the first ribonucleotide residue from the 5' end of the sense strand and the nineteenth ribonucleotide residue from the 5' end of the antisense strand are chemically modified in the chemical modification according to the conditions (i) to (vi), the nineteenth ribonucleotide residue from the 5' end of the antisense strand has not undergone chemical modification.

<Method of Chemical Modification>

The substitution (modification) method in which a fluoro group substitutes for the hydroxy group at the 2' position of the ribose moiety of each of cytidylic acid residues and uridylic acid residues and the substitution (modification) method in which a methoxy group substitutes for the hydroxy group at the 2' position of the ribose moiety of each of adenylic acid residues and guanylic acid residues are known, and therefore the chemically-modified siRNA of the present invention can be produced by a known technique.

2. SPG/Chemically-Modified siRNA Complex

The chemically-modified siRNA of the present invention is complexed with SPG to be used in the state of a schizophyllan/chemically-modified siRNA complex. SPG is a polysaccharide having a β-1,3-glucan structure, and bind to the above-described receptor Dectin-1 present on the cell surface, whereby the schizophyllan/chemically-modified siRNA complex is delivered into the cell by endocytosis.

Schizophyllan (also abbreviated as SPG in some cases) as a constituent of the SPG/chemically-modified siRNA complex can be produced according to a usual method described in a document (A.C.S. 38(1), 253(1997); Carbohydrate Research, 89, 121-135(1981)). By subjecting the thus-obtained schizophyllan to ultrasonic treatment, a desired molecular weight of schizophyllan can be obtained.

The molecular weight of schizophyllan used for the SPG/chemically-modified siRNA complex is not specifically restricted, but may be appropriately set depending on the chain length of polydeoxyadenylic acid added to the chemically-modified siRNA, etc. Concretely, the molecular weight of schizophyllan may be normally 25,000 to 500,000, preferably 25,000 to 250,000.

The SPG/chemically-modified siRNA complex can be prepared according to a known method of complexing SPG and polydeoxyadenylic acid. Concretely, a method of production according to the following steps (1) to (3) is exemplified: (1) a chemically-modified siRNA including polydeoxyadenylic acid is prepared in a known method, (2) SPG is separately prepared, and (3) using the polydeoxyadenylic acid bonded to the chemically-modified siRNA and SPG, a complex is formed.

In step (3) of the above method, the mixture ratio of the chemically-modified siRNA and SPG can be appropriately selected depending on the chain length of the polydeoxyadenylic acid and the molecular weight of SPG. In the SPG/chemically-modified siRNA complex, one molecule of glucose of the main chain of SPG corresponds to one deoxyadenylic acid residue of the polydeoxyadenylic acid, whereby one polydeoxyadenylic acid and two units of SPG take a triple helical structure. That is, in the SPG/chemically-modified siRNA complex, polydeoxyadenylic acid is taken in a double helical structure formed of two units of SPG at one location or two or more locations, forming a triple helical structure. For example, with a chemically-modified siRNA including polydeoxyadenylic acid having a base length of 40 and SPG having a molecular weight of 150000, it is possible to form a triple helical structure including two molecules of SPG having a molecular weight of 150000 and 17 molecules of the chemically-modified siRNA including polydeoxyadenylic acid having the base length. It is preferred that the chemically-modified siRNA including polydeoxyadenylic acid be mixed with SPG at a mole ratio of 20:1 to 1:5, preferably 10:1 to 1:1, to complex a single-stranded polydeoxyadenylic acid region bonded to the chemically-modified siRNA with SPG. By exposing the chemically-modified siRNA including polydeoxyadenylic acid and SPG at such a mole ratio under complex formation conditions, it is possible to make both constituents efficiently interact with each other and thus improve the production efficiency of the SPG/chemically-modified siRNA complex.

The triple helical structure of polydeoxyadenylic acid and SPG in the SPG/chemically-modified siRNA complex can be formed concretely according to the following method.

Naturally or in water, SPG takes a triple helical structure. This SPG is dissolved in a polar solvent such as dimethylsulfoxide (DMSO) or an alkaline aqueous solution such as a sodium hydroxide solution, to be denatured to a single strand. The chemically-modified siRNA including polydeoxyadenylic acid is then added to the resultant solvent or solution, and the solvent is put back in water or the alkaline aqueous solution is neutralized (renaturation process), thereby forming a structure complexed in a triple helical shape (association structure) constituted by a single-stranded moiety of the polydeoxyadenylic acid linked to the chemically-modified siRNA and two units of SPG. Such a complex of polydeoxyadenylic acid and a polysaccharide is considered formed mainly by way of hydrogen bonding and hydrophobic interaction.

The SPG/chemically-modified siRNA complex can inhibit expression of a target gene inside a cell by being introduced into the cell, and thus is usable as a medicinal composition intended to inhibit expression of a target gene. Such a medicinal composition can be prepared by containing the SPG/chemically-modified siRNA complex as an active ingredient by a therapeutically effective dose and further appropriately combining a pharmaceutically allowable carrier. Examples of such a carrier include: aqueous carriers such as purified water, a sugar-containing aqueous solution, a buffer solution, a saline solution, and nuclease-free water; and excipients.

The route of administration of the SPG/chemically-modified siRNA complex can be appropriately selected from methods conventionally used, such as the oral route, parenteral routes (including intravenous, intraperitoneal, intramuscular, subcutaneous, intrarectal, and intravaginal administration routes), inhalation, systemic administration, local administration (including external application to skin and a buccal cavity, and instillation to sites substantially free from invasion into a bloodstream, such as the eyes, the ears, and the nose), based on the symptom of the patient, the clinical state, the type of the disease, etc.

EXAMPLES

While the present invention will be described hereinafter in more detail based on examples, it should be noted that the present invention will not be restricted by these examples.

Production Example: Production of SPG/Chemically-Modified siRNA Complex

The SPG/chemically-modified siRNA complex used in the following experiment examples was formed in the following manner. SPG having a molecular weight of about 150000 was prepared in a 0.25 N sodium hydroxide solution to have the final concentration of 15 mg/ml. The solution was then stirred by vibration for one hour and left at rest at 4° C. for one day to be denatured. A solution of a chemically-modified siRNA having a given sequence with sulfurized polydeoxyadenylic acid added thereto, dissolved in 330 mM of primary sodium phosphate, was added to the denatured SPG solution, neutralized, and left at rest at 4° C. for 24 hours or longer. At this time, setting was made to have 0.27 mole of SPG with respect to one mole of the chemically-modified siRNA. Note that the chemically-modified siRNA with sulfurized polydeoxyadenylic acid added thereto refers to one in which 40 deoxyadenylic acids are linked to the 5' end of the sense strand of the siRNA by phosphoester bonding.

Reference Test Example 1

SPG/chemically-modified siRNA complexes were prepared using chemically-modified siRNAs (NJ050.11 and NJ050.13 shown in Table 3) for chemically modified CD40. Also, as a chemically-modified siRNA with no polydeoxyadenylic acid added thereto, NJ050.12 and NJ050.13 shown in Table 3 were prepared. The base sequences of the sense strand and antisense strand of the chemically-modified siRNAs respectively correspond to SEQ ID NOS: 1 and 2.

In NJ050.11, in the sense strand, a methoxy group has substituted for the hydroxy group at the 2' position of each of all adenylic acid residues and guanylic acid residues, and a fluoro group has substituted for the hydroxy group at the 2' position of each of all cytidylic acid residues and uridylic acid residues. In the antisense strand, a methoxy group has substituted for the hydroxy group at the 2' position of each of adenylic acid residues and guanylic acid residues at and after the eighth base from the 5' end, and a fluoro group has substituted for the hydroxy group at the 2' position of cytidylic acid residues and uridylic acid residues at and after the eighth base from the 5' end.

In NJ050.12, in both the sense and antisense strands, a fluoro group has substituted for the hydroxy group at the 2' position of each of cytidylic acid residues and uridylic acid residues in dinucleotide sequences constituted by CA, UA, and UG, and a methoxy group has substituted for the hydroxy group at the 2' position of each of adenylic acid residues and guanylic acid residues in such dinucleotide sequences.

In NJ050.13, in the sense strand, a fluoro group has substituted for the hydroxy group at the 2' position of each of cytidylic acid residues and uridylic acid residues in dinucleotide sequences constituted by CA, UA, and UG, and a methoxy group has substituted for the hydroxy group at the 2' position of each of adenylic acid residues and guanylic acid residues in such dinucleotide sequences. In the antisense strand, a methoxy group has substituted for the hydroxy group at the 2' position of each of adenylic acid residues and guanylic acid residues at and after the eighth base from the 5' end, and a fluoro group has substituted for the methoxy group at the 2' position of each of cytidylic acid residues and uridylic acid residues at and after the eighth base from the 5' end.

TABLE 3

| NJ050.1 1 |
| --- |
| Sense strand 5'→3': C(F)G(M)U(F)G(M)C(F)A(M)G(M)U(F)G(M)A(M)C(F)A(M)A(M)C(F)A(M)G(M)U(F)A(M)dtdt (SEQ ID NO: 15) |
| Antisense strand 5'→3': UACUGU(F)U(F)U(F)G(M)U(F)C(F)A(M)C(F)U(F)G(M)C(F)A(M)C(F)G(M)dtdt (SEQ ID NO: 16) |

TABLE 3-continued

NJ050.12

Sense strand 5'→3': CGU(F)G(M)C(F)A(M)GU(F)G(M)AC(F)A(M)AAC(F)A(M)GU(F)A(M)dtdt
(SEQ ID NO: 12)

Antisense strand 5'→3': U(F)A(M)CU(F)G(M)UUU(F)G(M)UC(F)A(M)CU(F)G(M)C(F)A(M)CGdtdt
(SEQ ID NO: 17)

NJ050.13

Sense strand 5'→3': CGU(F)G(M)C(F)A(M)GU(F)G(M)AC(F)A(M)AAC(F)A(M)GU(F)A(M)dtdt
(SEQ ID NO: 12)

Antisense strand 5'→3': UACUGUUU(F)G(M)UC(F)A(M)CU(F)G(M)C(F)A(M)CGdtdt
(SEQ ID NO: 14)

In Table, "dt", "U(F)", "G(M)", and "A(M)" are as defined in Table 1.

In Table, "dt", "U(F)", "G(M)", and "A(M)" are as defined in Table 1.

Each of the SPG/chemically-modified siRNA complexes and the chemically-modified siRNAs was introduced into 200,000 c-wrt-7LR cells (rat myelomonocytic leukemia-derived cells) by electroporation. After the introduction, the cells were seeded in a 48-well plate to have $2 \times 10^5$ cells/well, and incubated at 37° C. under 5% $CO_2$ for two hours. Thereafter, lipopolysaccharide (LPS) was added to each well to have 10 ng/mL, and incubated at 37° C. under 5% $CO_2$ for 22 hours. All RNAs were then extracted from the cells, and cDNA was synthesized from all RNAs. Using the synthesized cDNA as a template, real-time PCR was performed using a CD40 primer, to measure the mRNA amount of CD40. One subjected to LPS treatment without insertion of siRNA was used as a positive control, and one subjected to neither LPS treatment nor insertion of siRNA was used as a negative control. The mRNA amount of CD40 was corrected with the amount of 18SrRNA that is a house keeping gene.

The obtained results are shown in FIG. 1. In FIG. 1, "LPS(−)" denotes the negative control, "LPS(±)" denotes the positive control, "21 bp of NJ050.12" denotes the chemically-modified siRNA (base length: 21) of NJ050.12, "21 bp of NJ050.13" denotes the chemically-modified siRNA (base length: 21) of NJ050.13, "NJ050.11 (dA40-dsRNA)" denotes the SPG/chemically-modified siRNA complex using the chemically-modified siRNA of NJ050.11, and "NJ050.13 (dA40-dsRNA)" denotes the SPG/chemically-modified siRNA complex using the chemically-modified siRNA of NJ050.13.

From the above results, it was confirmed that the chemically-modified siRNA of NJ050.13 was lower in the mRNA amount of CD40 than the chemically-modified siRNA of NJ050.12, indicating that the gene expression inhibition effect enhanced when the first to seventh ribonucleotide residues from the 5' end of the antisense strand did not undergo chemical modification. On the other hand, no gene expression inhibition effect was recognized for the SPG/chemically-modified siRNA complex using the chemically-modified siRNA of NJ050.13.

Reference Test Example 2

As a cause of the fact that no gene expression inhibition effect was recognized for the SPG/chemically-modified siRNA complex using the chemically-modified siRNA of NJ050.13, considered was a possibility of incomplete uptake into RLC due to vulnerability of the base sequence. In this test, therefore, the stability of chemically-modified siRNAs and SPG/chemically-modified siRNA complexes in serum was evaluated.

The chemically-modified siRNA (naked) of NJ050.13 with 40 deoxyadenines linked to the 5' end of the sense strand by phosphoester bonding was added to RPMI1640 medium (Gibco) containing 10 mass % of fetal bovine serum (FBS) to have 1 μM, and incubated at 37° C. for 16 hours. Thereafter, TE saturated phenol/chloroform was added by the same amount as the specimen, strongly stirred by Vortex, and then centrifuged at 1200×g for 15 minutes. The supernatant was then recovered, the nucleic acid concentration of the supernatant was measured with a spectrophotometer, and the amount equivalent to 200 ng of nucleic acid was subjected to electrophoresis using 15% polyacrylamide gel. As a control, used was a dsRNA of NJ003.2 with 40 sulfurized polydeoxyadenylic acids linked to the 5' end of the sense strand by phosphoester bonding. The base sequence of the dsRNA of NJ003.2 is as shown in Table 4, and is known to be comparatively stable even in serum.

Testing was also performed for the SPG/chemically-modified siRNA complex using the chemically-modified siRNA of NJ050.13 and a SPG/siRNA complex using the dsRNA of NJ003.2 in a manner similar to that described above except that the nucleic acid amount subjected to electrophoresis was set to 400 ng.

Figure 2:
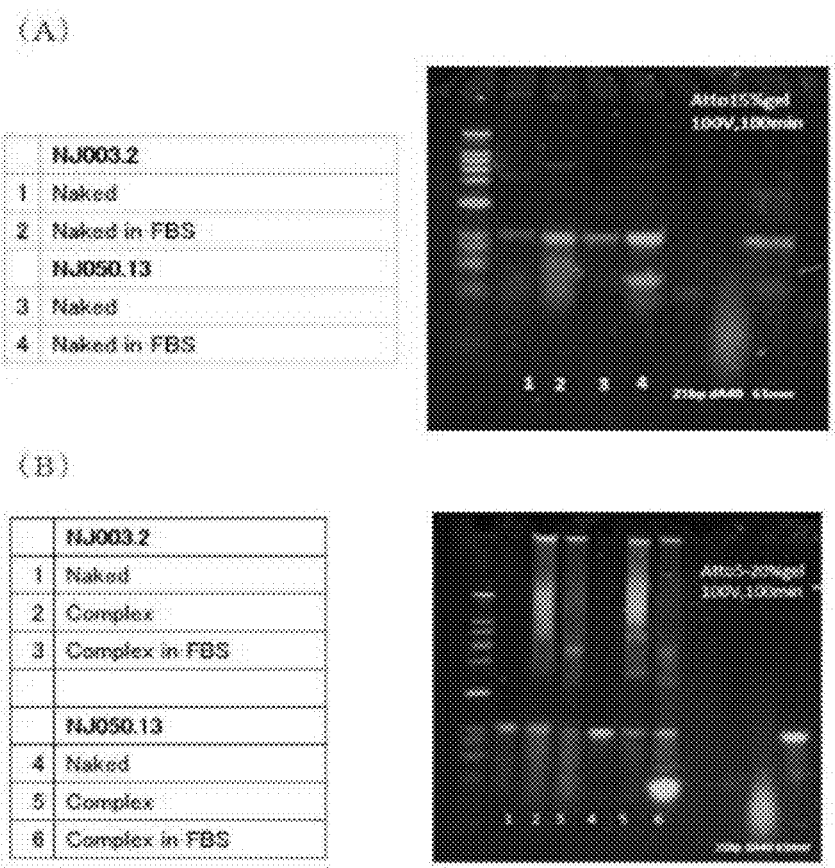
FIG. 2 shows the results of evaluation of stability in serum for various chemically-modified siRNAs and SPG/chemically-modified siRNA complexes using chemically-modified siRNAs in Reference Test Example 2.

The obtained results are shown in FIG. 2. In (A) of FIG. 2, the results of the chemically-modified siRNA of NJ050.13 (naked) and the chemically-modified siRNA of NJ050.13 (naked) are shown. In (A) of FIG. 2, "Naked" denotes the case where incubation was not performed under the presence of FBS, and "Naked-in-FBS" denotes the case where incubation was performed under the presence of FBS. In (B) of FIG. 2, the results of the SPG/chemically-modified siRNA complex using the chemically-modified siRNA of NJ050.13 and the SPG/siRNA complex using the dsRNA of NJ003.2 are shown. In (B) of FIG. 2, "Naked" denotes the case where the chemically-modified siRNA of NJ050.13 or the dsRNA of NJ003.2 was not incubated under the presence of FBS, "Complex" denotes the case where the SPG/chemically-modified siRNA complex or the SPG/siRNA complex was incubated under the presence of FBS, and "Complex-in-FBS" denotes the case where the SPG/chemically-modified siRNA complex or the SPG/siRNA complex was incubated under the presence of FBS.

From the above results, suggested was a possibility that the chemically-modified siRNA of NJ050.13 with sulfurized polydeoxyadenylic acid added to the 5' end of the sense strand might have been cleaved near the bonded site of the polydeoxyadenylic acid and the sense strand.

Reference Test Example 3

Since the necessity of enhancing the stability near the bonded site of the sulfurized polydeoxyadenylic acid and the sense strand of the siRNA was suggested from the results of Reference Test Example 2, it was decided to impart chemical modification to the bonded site of the sense strand. Also, since it was feared that the activity might be lost with the sense strand modification adopted in NJ050.11 from the results of Reference Test Example 1, a chemically modified siRNA of NJ050.14 shown in Table 4 was prepared.

TABLE 4

NJ050.14

Sense strand 5'→3': C(F)G(F)U F)G(F)C(F)A(M)G(F)U(F)G(F)A(F)C(F)A(M)A(F)A(M)C(M)A(F)G(F)U(F)A(M)dtdt (SEQ ID NO: 18)

Antisense strand 5'→3': UACUGUUU(F)G(M)UC(F)A(M)CU(F)G(M)C(F)A(M)CGdtdt (SEQ ID NO: 14)

In Table, "dt", "U(F)", "G(M)", and "A(M)" are as defined in Table 1.

In Table, "dt", "U(F)", "G(M)", and "A(M)" are as defined in Table 1.

dRAW cells (mouse macrophages; RAW264 cells excessively expressing Dectin-1) were seeded in a 48-well plate to have $2 \times 10^4$ cells/well and incubated at 37° C. under 5% $CO_2$ for 24 hours. Thereafter, a SPG/chemically-modified siRNA complex was added to have 200 nM or 400 nM, and incubated at 37° C. under 5% $CO_2$ for 12 hours. Interferon γ (IFNr) was then added to each well to have 0.2 ng/mL, and incubated at 37° C. under 5% $CO_2$ for four hours. All RNAs were then extracted from the cells, and cDNA was synthesized from all RNAs. Using the synthesized cDNA as a template, real-time PCR was performed using a CD40 primer, to measure the mRNA amount of CD40. One subjected to IFNr treatment without addition of the SPG/chemically-modified siRNA complex was used as a positive control, and one subjected to neither IFNr treatment nor addition of the SPG/chemically-modified siRNA complex was used as a negative control. The mRNA amount of CD40 was corrected with the amount of 18SrRNA that is a house keeping gene.

Figure 3:
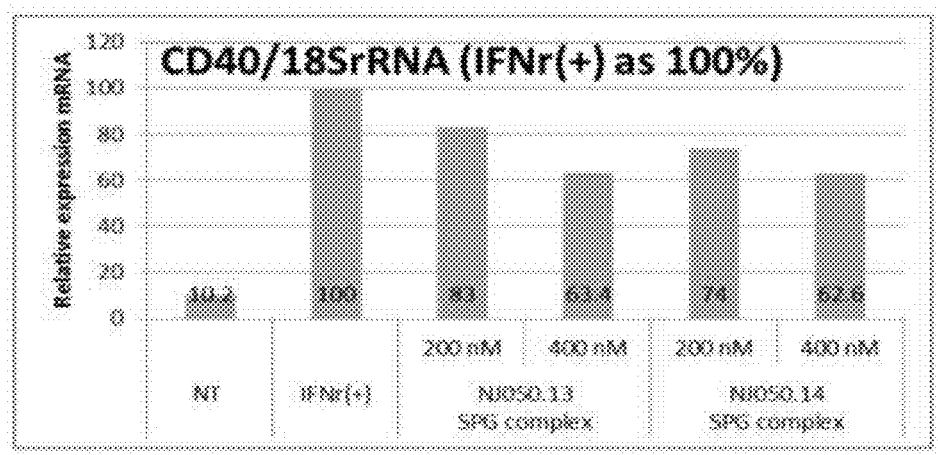
FIG. 3 shows the results of evaluation of the gene expression inhibition effect for SPG/chemically-modified siRNA complexes using various chemically-modified siRNAs in Reference Test Example 3.

The obtained results are shown in FIG. 3. In FIG. 3, "NT" denotes the negative control, "IFNγ(+)" denotes the positive control, "NJ050.13 SPG complex" denotes the SPG/chemically-modified siRNA complex using the chemically-modified siRNA of NJ050.13, and "NJ050.14 SPG complex" denotes the SPG/chemically-modified siRNA complex using the chemically-modified siRNA of NJ050.14. From the above results, it was confirmed that the SPG/chemically-modified siRNA complex using the chemically-modified siRNA of NJ050.14 had a good gene expression inhibition effect comparable to the complex using the chemically-modified siRNA of NJ050.13.

Reference Test Example 4

The SPG/chemically-modified siRNA complex using the chemically-modified siRNA of NJ050.14, 200 ng, was added to serum (mouse serum, human serum, and FBS), and incubated at 37° C. for one minute or 30 minutes. Thereafter, TE saturated phenol/chloroform was added by the same volume as the specimen, strongly stirred by Vortex, and then centrifuged at 1200×g for 15 minutes. The supernatant was then recovered, the nucleic acid concentration of the supernatant was measured with a spectrophotometer, and the amount equivalent to 200 ng of nucleic acid was subjected to electrophoresis using 15% polyacrylamide gel.

Figure 4:
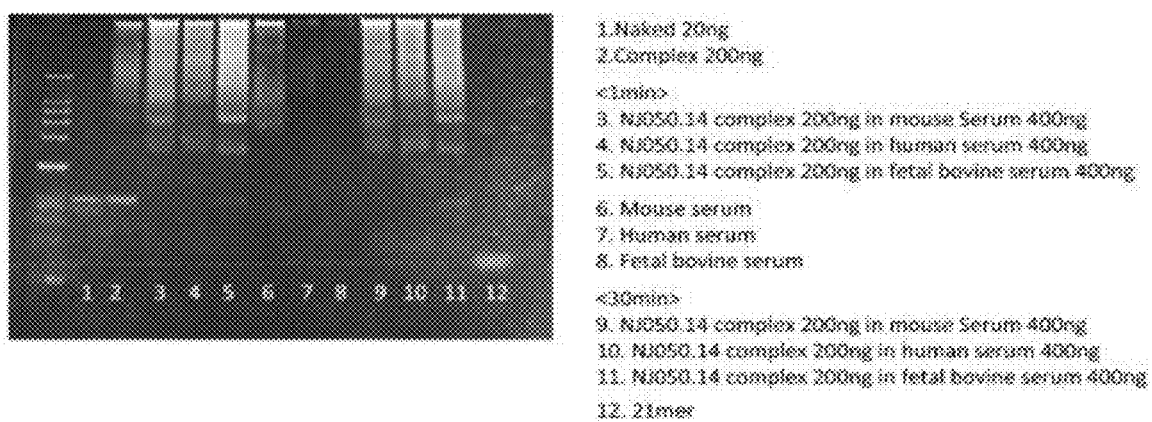
FIG. 4 shows the results of evaluation of stability in serum for SPG/chemically-modified siRNA complexes using various chemically-modified siRNAs in Reference Test Example 4.

The obtained results are shown in FIG. 4. In FIG. 4, "Naked" in lane 1 denotes the case where the chemically-modified siRNA of NJ050.13 with sulfurized polydeoxyadenylic acid added thereto was not incubated under the presence of serum, "Complex" in lane 2 denotes the case where the SPG/chemically-modified siRNA complex using the chemically-modified siRNA of NJ050.14 was not incubated under the presence of serum, "NJ050.14 complex" in lanes 3 to 5 and 9 to 11 denotes the SPG/chemically-modified siRNA complex using the chemically-modified siRNA of NJ050.14, and "21mer" in lane 12 denotes the sense strand sequence of a chemically-modified siRNA moiety of NJ003.2 and was used as a size marker. From these results, it was confirmed that the SPG/chemically-modified siRNA complex using the chemically-modified siRNA of NJ050.14 was comparatively stable under the presence of serum.

Test Example 1

The chemically-modified siRNA of NJ050.14 has many locations where a methoxy group has substituted for the hydroxy group at the 2' position of each of adenylic acid residues and guanylic acid residues, and therefore it is feared that the yield may decrease in production. Also, while the chemically-modified siRNA of NJ050.14 is comparatively stable under the presence of serum, it is less stable in serum than the chemically-modified siRNA of NJ050.13 and considered not enduring in-vivo use. In view of this, while the chemical modification to the bonded sites of the sulfurized polydeoxyadenylic acid and the sense strand of the siRNA is indispensable, it is necessary to reduce the number of chemical modifications to the extent possible even at the expense of stability and develop a chemically-modified siRNA having a suitable gene expression inhibition effect.

In consideration of the above, a chemically modified siRNA of NJ050.15 shown in Table 5 was prepared. The chemically modified siRNA of NJ050.15 satisfies the conditions (i) to (ix) defined according to the present invention.

TABLE 5

NJ050.15 (A-3 modification)

Sense strand 5'→3': C(F)GU(F)G(M)C(F)A(M)GU(F)G(M)AC(F)A(M)AAC(F)A(M)GU(F)A(M)dtdt (SEQ ID NO: 19)

TABLE 5-continued

NJ050.15 (A-3 modification)

Antisense strand 5'→3': UACUGUUU(F)G(M)UC(F)A(M)CU(F)G(M)C(F)A(M)CGdtdt
(SEQ ID NO: 14)

In Table, "dt", "U(F)", "G(M)", and "A(M)" are as defined in Table 1.

In Table, "dt", "U(F)", "G(M)", and "A(M)" are as defined in Table 1.

dRAW cells (mouse macrophages; RAW264 cells excessively expressing Dectin-1) were seeded in a 48-well plate to have 5×10$^4$ cells/well. Simultaneously, 200 nM of a SPG/chemically-modified siRNA complex (using the chemically-modified siRNA of NJ050.14 and NJ050.15) and 0.2 ng/mL of interferon γ (IFNr) were added, and incubated at 37° C. under 5% $CO_2$ for 24 hours. Thereafter, all RNAs were extracted from the cells, and cDNA was synthesized from all RNAs. Using the synthesized cDNA as a template, real-time PCR was performed using a CD40 primer, to measure the mRNA amount of CD40. One subjected to IFNr treatment without addition of the SPG/chemically-modified siRNA complex was used as a positive control, and one subjected to neither IFNr treatment nor addition of the SPG/chemically-modified siRNA complex was used as a negative control. The mRNA amount of CD40 was corrected with the amount of 18SrRNA that is a house keeping gene. For comparison, testing was performed in a similar manner using the chemically-modified siRNAs of NJ050.14 and NJ050.15 with sulfurized polydeoxyadenylic acid added thereto.

Figure 5:
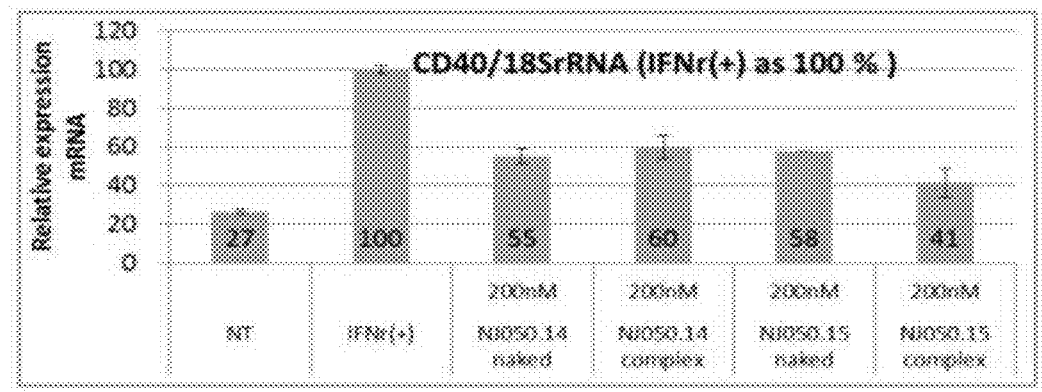
FIG. 5 shows the results of evaluation of the gene expression inhibition effect for various chemically-modified siRNAs and SPG/chemically-modified siRNA complexes using chemically-modified siRNAs in Test Example 1.

The obtained results are shown in FIG. 5. In FIG. 5, "NT" denotes the negative control, "IFNγ(+)" denotes the positive control, "NJ050.14 naked" denotes the chemically-modified siRNA of NJ050.14 with 40 deoxyadenines linked to the 5' end of the sense strand by phosphoester bonding, "NJ050.14 complex" denotes the SPG/chemically-modified siRNA complex using the chemically-modified siRNA of NJ050.14, "NJ050.15 naked" denotes the chemically-modified siRNA of NJ050.15 with 40 deoxyadenylic acids linked to the 5' end of the sense strand by phosphoester bonding, and "NJ050.15 complex" denotes the SPG/chemically-modified siRNA complex using the chemically-modified siRNA of NJ050.15. From the above results, it was confirmed that the SPG/chemically-modified siRNA complex using the chemically-modified siRNA of NJ050.15 had a comparable or good gene expression inhibition effect compared to the SPG/chemically-modified siRNA complex using the chemically-modified siRNA of NJ050.14.

Test Example 2

The stability in serum was evaluated for the SPG/chemically-modified siRNA complex using the chemically-modified siRNA of NJ050.14 or NJ050.15 and SPG/chemically-modified siRNA complexes using chemically-modified siRNAs shown in Table 6. Concretely, each of the SPG/chemically-modified siRNA complexes was added to serum (human serum and FBS) to have 1 μM, and incubated at 37° C. for 16 hours. Thereafter, TE saturated phenol/chloroform was added by the same amount as the specimen, strongly stirred by Vortex, and then centrifuged at 1200×g for 15 minutes. The supernatant was then recovered, the nucleic acid concentration of the supernatant was measured with a spectrophotometer, and the amount equivalent to 20 ng of nucleic acid was subjected to electrophoresis using 15% polyacrylamide gel. Undegraded chemically-modified siRNAs were quantified using Image J analysis software, to obtain the residual ratio (%).

TABLE 6

NJ070.13

Sense strand 5'→3': C(M)GGUGAAAGCGAAUUCCUAUU (SEQ ID NO: 20)

Antisense strand 5'→3': UAGGAAUUCGCUUUCACCGUU (SEQ ID NO: 21)

NJ070.13t

Sense strand 5'→3': C(M)GGUGAAAGCGAAUUCCUdtdt (SEQ ID NO: 22)

Antisense strand 5'→3': UAGGAAUUCGCUUUCACCGdtdt (SEQ ID NO: 23)

NJ070.14 (A-3 modification)

Sense strand 5'→3': C(F)GGU(F)G(M)AAAGCGAAUUCCU(F)A(M)dtdt
(SEQ ID NO: 24)

Antisense strand 5'→3': UAGGAAUUCGCUUUC(F)A(M)CCGdtdt (SEQ ID NO: 25)

NJ151A3 (A-3 modification)

Sense strand 5'→3': C(F)A(M)U(F)G(M)C(F)A(M)GAGAAAAAC(F)A(M)GU(F)A(M)dtdt
(SEQ ID NO: 26)

Antisense strand 5'→3': UACUGUUUUCUCU(F)G(M)C(F)A(M)U(F)Gdtdt
(SEQ ID NO: 27)

TABLE 6-continued

NJ003.2

Sense strand 5'→3': GGAGGGCACCGCAGAAUCAUU (SEQ ID NO: 28)

Antisense strand 5'→3': UGAUUCUGCGGUGCCCUCCUU (SEQ ID NO: 29)

NJ003.21 (A-3 modification)

Sense strand 5'→3': G(M)GAGGGC(F)A(M)CCGC(F)A(M)GAAUC(F)A(M)UUdtdt
(SEQ ID NO: 30)

Antisense strand 5'→3': UGAUUCUG(M)CGGU(F)G(M)CCCUCCdtdt
(SEQ ID NO: 31)

Figure 6:
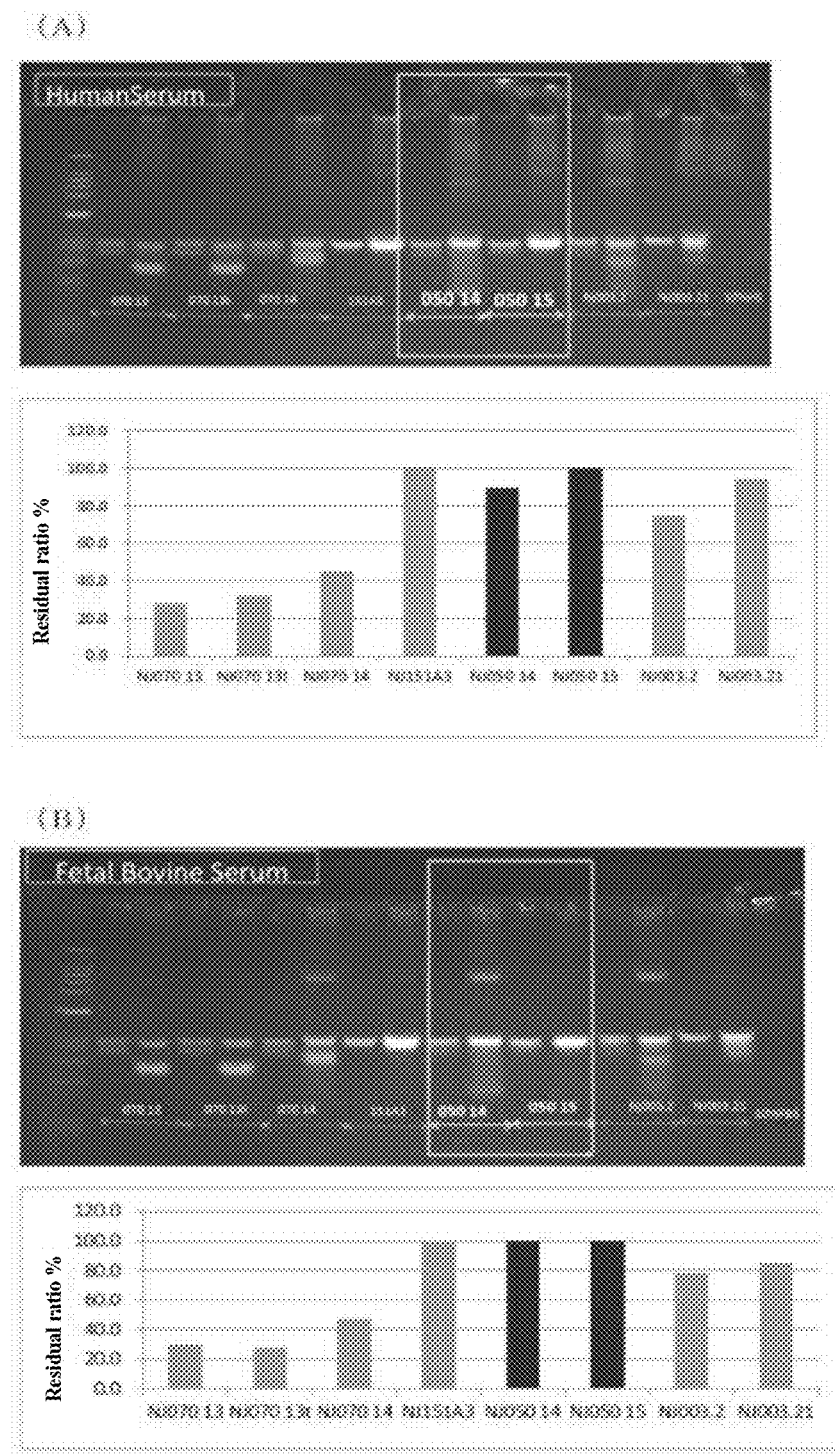
FIG. 6 shows the results of evaluation of stability in serum for SPG/chemically-modified siRNA complexes using various modified siRNAs in Test Example 2.

The obtained results are shown in FIG. 6, in which (A) shows the results obtained using human serum and (B) shows the results obtained using FBS. Surprisingly, the SPG/chemically-modified siRNA complex using the chemically-modified siRNA of NJ050.15 had comparable or good stability compared to the complex using NJ050.14 in spite of its reduced number of chemical modifications.

Test Example 3

Using the SPG/chemically-modified siRNA complex using the chemically-modified siRNA of NJ050.14 or NJ050.15, an x-vivo MLR (mixed lymphocyte culture) assay was performed, to evaluate the cell proliferation inhibition effect. Concretely, the SPG/chemically-modified siRNA complex using the chemically-modified siRNA of NJ050.14 or NJ050.15 was administered into BALB/c mice (male, 9 weeks old) by tail vein injection to have 0.2 µg/head or 2 µg/head. After the lapse of 20 hours, spleens were harvested from the BALB/c mice, and spleen cells (5×10$^6$ cells/mL) were prepared according to a usual method. The resultant spleen cells were exposed to 15 Gy radiation for inactivation treatment, to prepare stimulator cells. Separately, spleens of C57BL/6 mice (male, 9 weeks old) were harvested, and spleen cells (5×10$^6$ cells/mL) were prepared according to a usual method, to prepare responder cells. The stimulator cells and the responder cells, each 100 µL, were put in each well of a 96-well plate and subjected to mixed lymphocyte reaction (MLR) at 37° C. under 5% $CO_2$ for 96 hours. After the reaction, cell proliferation was measured using Cell Proliferation ELISA, BrdU kit (Roche Lifescience). Note that one using PBS in place of the SPG/chemically-modified siRNA complex was used as a control.

Figure 7:
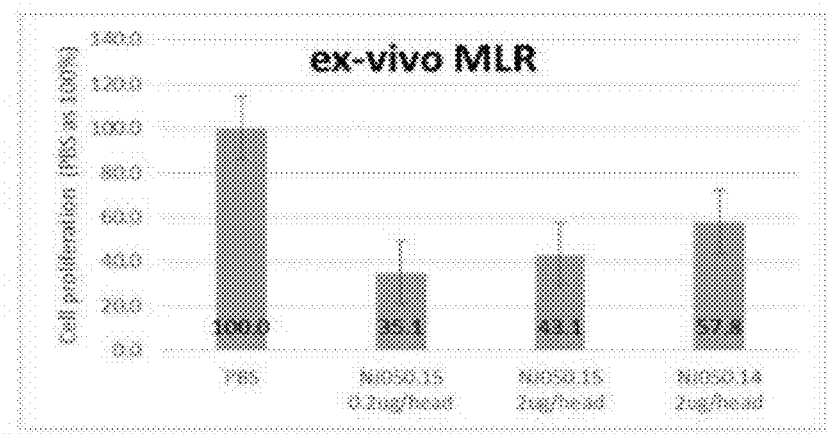
FIG. 7 shows the results of evaluation of the cell proliferation inhibition effect by an ex-vivo MLR (mixed lymphocyte culture) assay for SPG/chemically-modified siRNA complexes using various modified siRNAs in Test Example 3.

The obtained results are shown in FIG. 7. From the results, it was confirmed that the SPG/chemically-modified siRNA complex using the chemically-modified siRNA of NJ050.15 was capable of improving the stability and also inducing high knock-down activity with smaller chemical modification.

Test Example 4

SPG/chemically-modified siRNA complexes were prepared using siRNAs chemically modified under a specific rule (siRNAs for CD40, for human sequences). Concretely, prepared were ones with 40 sulfurized deoxyadenylic acids linked to the 5' end of the sense strand of various chemically-modified siRNAs shown in Table 7 by phosphoester bonding, to prepare various SPG/chemically-modified siRNA complexes in the manner described above. Note that the base sequences of the sense strand and antisense strand of hsiCD40(208) shown in Table 7 respectively correspond to SEQ ID NOS: 3 and 4, the base sequences of the sense strand and antisense strand of hsiCD40(867) respectively correspond to SEQ ID NOS: 5 and 6, and the base sequences of the sense strand and antisense strand of hsiCD40(1019) respectively correspond to SEQ ID NOS: 7 and 8, and the base sequences of the sense strand and antisense strand of hsiCD40(998) respectively correspond to SEQ ID NOS: 9 and 10.

Chemical modification pattern A-1 shown in Table 7 is a modification pattern having comparatively high stability and strong activity found as a result of examinations on the stability of complexes of siRNAs with previously sulfurized polydeoxyadenine added thereto and SPG. In the chemical modification pattern A-1, in the sense strand, a fluoro group has substituted for the hydroxy group at the 2' position of each of the first, second, third, fourth, fifth, seventh, eighth, ninth, tenth, eleventh, thirteenth, sixteenth, seventeenth, and eighteenth ribonucleotide residues from the 5' end, and a methoxy group has substituted for the hydroxy group at the 2' position of each of the sixth, twelfth, fourteenth, fifteenth, and nineteenth ribonucleotide residues from the 5' end of the sense strand. Also, in the chemical modification pattern A-1, in the antisense strand, a fluoro group has substituted for the hydroxy group at the 2' position of each of cytidylic acid residues and uridylic acid residues in dinucleotide sequences constituted by CA, UA, and UG, and a methoxy group has substituted for the hydroxy group at the 2' position of each of adenylic acid residues and guanylic acid residues in such dinucleotide sequences.

In chemical modification pattern A-2 shown in Table 7, in the sense strand, a fluoro group has substituted for the hydroxy group at the 2' position of all cytidylic acid residues and uridylic acid residues, and a methoxy group has substituted for the hydroxy group at the 2' position of all adenylic acid residues and guanylic acid residues. Also, in the chemical modification pattern A-2, in the antisense strand, a fluoro group has substituted for the hydroxy group at the 2' position of cytidylic acid residues and uridylic acid residues in dinucleotide sequences constituted by CA, UA, and UG, and a methoxy group has substituted for the hydroxy group at the 2' position of adenylic acid residues and guanylic acid residues in such dinucleotide sequences.

Chemical modification pattern A-3 shown in Table 7 satisfies the conditions (i) to (ix) defined according to the present invention.

TABLE 7

| | Chemical modification pattern | Sequence |
|---|---|---|
| hsiCD40 (208) | A-1 | Sense strand 5'→3': G(F)A(F)C(F)A(F)G(F)A(M)A(F)A(F)C(F)U(F)G(F)G(M)U(F)G(M)A(M)G(F)U(F)G(F)A(M)dtdt (SEQ ID NO: 32)<br>Antisense strand 5'→3': UCACUCACC(F)A(M)GUUUCU(F)G(M)UCdtdt (SEQ ID NO: 33) |
| | A-2 | Sense strand 5'→3': G(M)A(M)C(F)A(M)G(M)A(M)A(M)A(M)A(M)C(F)U(F)G(M)G(M)U(F)G(M)A(M)G(M)U(F)G(M)A(M)dtdt (SEQ ID NO: 34)<br>Antisense strand 5'→3': UCACUCACC(F)A(M)GUUUCU(F)G(M)UCdtdt (SEQ ID NO: 33) |
| | A-3 | Sense strand 5'→3': G(M)A(M)C(F)A(M)GAAACU(F)G(M)GU(F)G(M)AGU(F)G(M)Adtdt (SEQ ID NO: 35)<br>Antisense strand 5'→3': UCACUCACC(F)A(M)GUUUCU(F)G(M)UCdtdt (SEQ ID NO: 33) |
| hsiCD40 (867) | A-1 | Sense strand 5'→3': A(F)G(F)U(F)G(F)U(F)G(M)G(F)C(F)C(F)A(F)C(F)G(M)U(F)G(M)(3(M)G(F)C(F)A(F)A(M)dtdt (SEQ ID NO: 36)<br>Antisense strand 5'→3': UUGCCCACGU(F)G(M)GCC(F)A(M)C(F)A(M)CUdtdt (SEQ ID NO: 37) |
| | A-2 | Sense strand 5'→3': A(M)G(M)U(F)G(M)U(F)G(M)G(M)C(F)C(F)A(M)C(F)G(M)U(F)G(M)G(M)G(M)C(F)A(M)A(M)dtdt (SEQ ID NO: 38)<br>Antisense strand 5'→3': UUGCCCACGU(F)G(M)GCC(F)A(M)C(F)A(M)CUdtdt (SEQ ID NO: 37) |
| | A-3 | Sense strand 5'→3': A(M)GU(F)G(M)U(F)G(M)GCC(F)A(M)CGU(F)G(M)GGC(F)A(M)Adtdt (SEQ ID NO: 39)<br>Antisense strand 5'→3': UUGCCACGU(F)G(M)GCC(F)A(M)C(F)A(M)CUdtdt (SEQ ID NO: 37) |
| hsiCD40 (1019) | A-1 | Sense strand 5'→3': C(F)A(F)G(F)A(F)A(F)A(M)C(F)A(F)G(F)U(F)U(F)C(M)A(F)C(M)C(M)U(F)U(F)G(F)A(M)dtdt (SEQ ID NO: 40)<br>Antisense strand 5'→3': UCAAGGUGAACU(F)G(M)UUUCU(F)Gdtdt (SEQ ID NO: 41) |
| | A-2 | Sense strand 5'→3': C(F)A(M)G(M)A(M)A(M)A(M)C(F)A(M)G(M)U(F)U(F)C(F)A(M)C(F)C(F)U(F)U(F)G(M)A(M)dtdt (SEQ ID NO: 42)<br>Antisense strand 5'→3': UCAAGGU(F)G(M)AACU(F)G(M)UUUCU(F)Gdtdt (SEQ ID NO: 43) |
| | A-3 | Sense strand 5'→3': C(F)AGA(M)AAC(F)A(M)GUUC(F)A(M)CCUU(F)G(M)Adtdt (SEQ ID NO: 44)<br>Antisense strand 5'→3': UCAAGGU(F)G(M)AACU(F)G(M)UUUCU(F)Gdtdt (SEQ ID NO: 45) |
| hsiCD40 (998) | A-3 | Sense strand 5'→3': C(F)A(M)GGAGACCU(F)G(M)GC(F)A(M)CU(F)G(M)GAdtdt (SEQ ID NO: 46)<br>Antisense strand 5'→3': UCCAGUGCC(F)A(M)GGUCUCCU(F)Gdtdt (SEQ ID NO: 47) |

In Table, "dt", "U(F)", "G(M)", and "A(M)" are as defined in Table 1.

In Table, "dt", "U(F)", "G(M)", and "A(M)" are as defined in Table 1.

Each of the SPG/chemically-modified siRNA complexes, 400 nM, was introduced into 500,000 human peripheral blood mononuclear cells (PBMC) by electroporation. After the introduction, the cells were seeded in a 48-well plate to have 2×10⁵ cells/well. Simultaneously, TNFα was added to have 2.5 ng/mL, and incubation was made at 37° C. under 5% $CO_2$ for 24 hours. All RNAs were then extracted from the cells, and cDNA was synthesized from all RNAs. Using the synthesized cDNA as a template, real-time PCR was performed using a CD40 primer, to measure the mRNA amount of CD40. One subjected to LPS treatment without insertion of siRNA was used as a positive control, and one subjected to neither LPS treatment nor insertion of siRNA was used as a negative control. Analysis of the results was performed by a ΔΔCT method, and the mRNA amount of CD40 was corrected with the amount of GAPDH that is a house keeping gene. Also, for comparison, testing was performed in a similar manner using a SPG/siRNA complex using a chemically unmodified siRNA and various chemically-modified siRNAs each with 40 sulfurized deoxyadenylic acids linked to the 5' end of the sense strand by phosphoester bonding, in place of the SPG/chemically-modified siRNA complexes.

Figure 8:
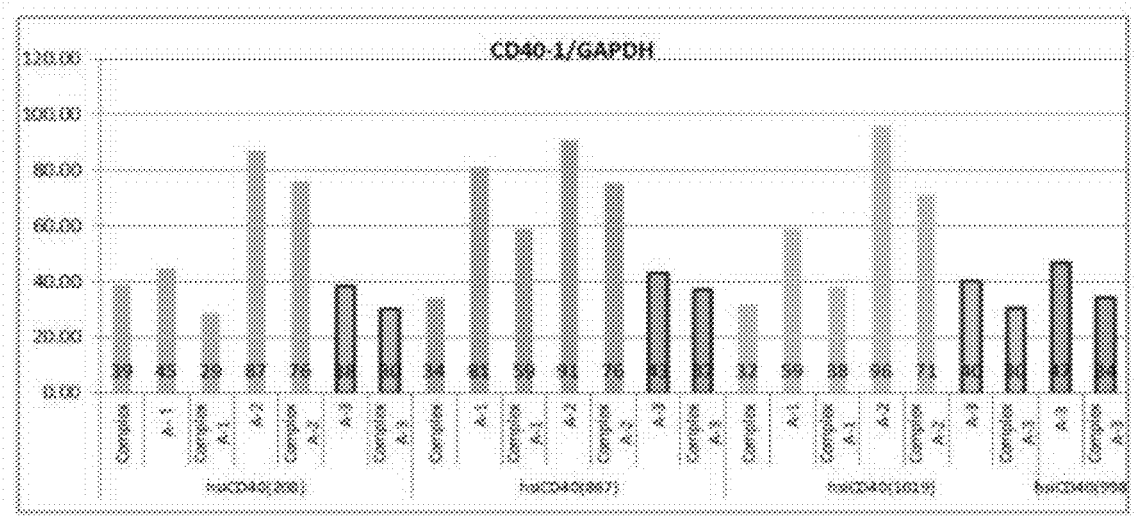
FIG. 8 shows the results of evaluation of the gene expression inhibition effect for various chemically-modified siRNAs and SPG/chemically-modified siRNA complexes using chemically-modified siRNAs in Test Example 4.

The obtained results are shown in FIG. 8. In FIG. 8, "Complex" denotes the SPG/siRNA complex using the chemically unmodified siRNA, "A-1" denotes a chemically-modified siRNA subjected to the chemical modification pattern A-1 with 40 sulfurized deoxyadenylic acids linked to the 5' end of the sense strand by phosphoester bonding, "Complex A-1" denotes a SPG/chemically-modified siRNA complex using the chemically-modified siRNA subjected to the chemical modification pattern A-1, "A-2" denotes a chemically-modified siRNA subjected to the chemical modification pattern A-2 with 40 sulfurized deoxyadenylic acids linked to the 5' end of the sense strand by phosphoester bonding, "Complex A-2" denotes a SPG/chemically-modified siRNA complex using the chemically-modified siRNA subjected to the chemical modification pattern A-2, "A-3" denotes a chemically-modified siRNA subjected to the chemical modification pattern A-3 with 40 sulfurized deoxyadenylic acids linked to the 5' end of the sense strand by phosphoester bonding, and "Complex A-3" denotes a SPG/chemically-modified siRNA complex using the chemically-modified siRNA subjected to the chemical modification pattern A-3. From the above results, it was found that the gene expression inhibition effect was highest when the SPG/chemically-modified siRNA complexes using the chemically-modified siRNAs subjected to the chemical modification pattern A-3 were used.

From the results of Test Examples 1 to 4, it has been clarified that the SPG/chemically-modified siRNA complexes using the chemically-modified siRNAs subjected to the chemical modification satisfying the conditions (i) to (ix) defined according to the present invention are high in both resistance against RNase and RNAi activity and can exert a sufficient gene expression inhibition effect even in in-vivo use.

The invention claimed is:

1. A chemically-modified siRNA with polydeoxyadenylic acid added to a 5' end of a sense strand, wherein
a base sequence of the sense strand includes at least one kind of dinucleotide sequence selected from the group consisting of CA, UA, and UG, and
a base sequence beginning at or after the eighth base from a 5' end of an antisense strand includes at least one kind of dinucleotide sequence selected from the group consisting of CA, UA, and UG, and
conditions (i) to (ix) below are satisfied:
(i) when the dinucleotide sequence constituted by CA is included in the base sequence of the sense strand, a fluoro group is substituted for the 2' hydroxy group of a cytidylic acid residue in the dinucleotide sequence, and a methoxy group is substituted for the 2' hydroxy group of an adenylic acid residue in the dinucleotide sequence;
(ii) when the dinucleotide sequence constituted by UA is included in the base sequence of the sense strand, a fluoro group is substituted for the 2' hydroxy group of a uridylic acid residue in the dinucleotide sequence, and a methoxy group is substituted for the 2' hydroxy group of an adenylic acid residue in the dinucleotide sequence;
(iii) when the dinucleotide sequence constituted by UG is included in the base sequence of the sense strand, a fluoro group is substituted for the 2' hydroxy group of a uridylic acid residue in the dinucleotide sequence, and a methoxy group is substituted for the 2' hydroxy group of a guanylic acid residue in the dinucleotide sequence;
(iv) when the dinucleotide sequence constituted by CA is included in the base sequence beginning at or after the eighth base from the 5' end of the antisense strand, a fluoro group is substituted for the 2' hydroxy group of a cytidylic acid residue in the dinucleotide sequence, and a methoxy group is substituted for the 2' hydroxy group of an adenylic acid residue in the dinucleotide sequence;
(v) when the dinucleotide sequence constituted by UA is included in the base sequence at or after the eighth base from the 5' end of the antisense strand, a fluoro group is substituted for the 2' hydroxy group of a uridylic acid residue in the dinucleotide sequence, and a methoxy group is substituted for the 2' hydroxy group of an adenylic acid residue in the dinucleotide sequence;
(vi) when the dinucleotide sequence constituted by UG is included in the base sequence beginning at or after the eighth base from the 5' end of the antisense strand, a fluoro group is substituted for the 2' hydroxy group of a uridylic acid residue in the dinucleotide sequence, and a methoxy group is substituted for the 2' hydroxy group of a guanylic acid residue in the dinucleotide sequence;
(vii) the first to seventh ribonucleotide residues from the 5' end of the antisense strand have not undergone chemical modification;
(viii) when neither the first ribonucleotide residue from the 5' end of the sense strand nor the nineteenth ribonucleotide residue from the 5' end of the antisense strand is chemically modified in the chemical modification according to the conditions (i) to (vi), if the first ribonucleotide residue from the 5' end of the sense strand is a cytidylic acid residue or a uridylic acid residue, a fluoro group is substituted for the 2' hydroxy group, and if the ribonucleotide residue is an adenylic acid residue or a guanylic acid residue, a methoxy group is substituted for the 2' hydroxy group; and
(ix) with the proviso that if the first ribonucleotide residue from the 5' end of the sense strand is chemically modified in the chemical modification according to any one of the conditions (i) to (iii), the nineteenth ribonucleotide residue from the 5' end of the antisense strand has not undergone chemical modification according to conditions (iv) to (vi).

2. The chemically-modified siRNA according to claim 1, wherein the polydeoxyadenylic acid has a length of 10 to 100 bases.

3. A schizophyllan/chemically-modified siRNA complex, wherein the chemically-modified siRNA according to claim 1 is complexed with schizophyllan.

4. The chemically-modified siRNA according to claim 1, wherein the base sequence of the sense strand includes the dinucleotide sequence CA.

5. The chemically-modified siRNA according to claim 1, wherein the base sequence of the sense strand includes the dinucleotide sequence UA.

6. The chemically-modified siRNA according to claim 1, wherein the base sequence of the sense strand includes the dinucleotide sequence UG.

7. The chemically-modified siRNA according to claim 1, wherein the base sequence beginning at or after the eighth base from the 5' end of the antisense strand includes the dinucleotide sequence CA.

8. The chemically-modified siRNA according to claim 1, wherein the base sequence beginning at or after the eighth base from the 5' end of the antisense strand includes the dinucleotide sequence UA.

9. The chemically-modified siRNA according to claim 1, wherein the base sequence beginning at or after the eighth base from the 5' end of the antisense strand includes the dinucleotide sequence UG.

10. A chemically-modified siRNA, comprising a sense strand and an antisense strand having the sequences:
Sense strand:5':
-C(F)GU(F)G(M)C(F)A(M)GU(F)G(M)AC(F)A(M) AAC(F)A(M)GU(F)A(M)dtdt-3' (SEQ ID NO: 19)
Antisense strand:
5'-UACUGUUU(F)G(M)UC(F)A(M)CU(F)G(M)C(F)A (M)CGdtdt-3' (SEQ ID NO: 14)
wherein, dt denotes a deoxythymidylic acid residue, U(F) denotes an uridylic acid residue where the 2' hydroxy group has been replaced with a fluoro group, G(M) denotes a guanylic acid residue where a methoxy group has been substituted for the 2' hydroxy group, C(F) denotes a cytidylic acid residue where the 2' hydroxy group has been replaced with a fluoro group, and A(M) denotes an adenylic acid residue where a methoxy group has been substituted for the 2' hydroxy group, and
wherein the sense strand has a polydeoxyadenylic acid sequence at the 5' end.

11. The chemically-modified siRNA according to claim 10, wherein the polydeoxyadenylic acid sequence has a length of 40 bases, and phosphodiester bonds of the polydeoxyadenylic acid are phosphorothioated.

12. A schizophyllan/chemically-modified siRNA complex, wherein the chemically-modified siRNA according to claim 11 is complexed with schizophyllan.

13. A chemically-modified siRNA, comprising a sense strand and an antisense strand having the sequences:
Sense strand:
5'-G(M)A(M)C(F)A(M)GAAACU(F)G(M)GU(F)G(M) AGU(F)G(M)Adtdt-3' (SEQ ID NO: 35)
Antisense strand:
5'-UCACUCACC(F)A(M)GUUUCU(F)G(M)UCdtdt-3' (SEQ ID NO: 33)
wherein, dt denotes a deoxythymidylic acid residue, U(F) denotes a uridylic acid residue where the 2' hydroxy group has been replaced with a fluoro group, G(M) denotes a guanylic acid residue where a methoxy group has been substituted for the 2' hydroxy group, C(F) denotes a cytidylic acid residue where the 2' hydroxy group has been replaced with a fluoro group, and A(M) denotes an adenylic acid residue where a methoxy group has been substituted for the 2' hydroxy group, and
wherein the sense strand has a polydeoxyadenylic acid sequence at the 5' end.

14. The chemically-modified siRNA according to claim 13, wherein the polydeoxyadenylic acid sequence has a length of 40 bases, and phosphodiester bonds of the polydeoxyadenylic acid are phosphorothioated.

15. A schizophyllan/chemically-modified siRNA complex, wherein the chemically-modified siRNA according to claim 14 is complexed with schizophyllan.

16. A chemically-modified siRNA, comprising a sense strand and an antisense strand having the sequences:
Sense strand:
5'-A(M)GU(F)G(M)U(F)G(M)GCC(F)A(M)CGU(F)G (M)GGC(F)A(M)Adtdt-3' (SEQ ID NO: 39)
Antisense strand:
5'-UUGCCCACGU(F)G(M)GCC(F)A(M)C(F)A(M) CUdtdt-3' (SEQ ID NO: 37)
wherein, dt denotes a deoxythymidylic acid residue, U(F) denotes a uridylic acid residue where the 2' hydroxy group has been replaced with a fluoro group, G(M) denotes a guanylic acid residue where a methoxy group has been substituted for the 2' hydroxy group, C(F) denotes a cytidylic acid residue where the 2' hydroxy group has been replaced with a fluoro group, and A(M) denotes an adenylic acid residue where a methoxy group has been substituted for the 2' hydroxy group, and
wherein the sense strand has a polydeoxyadenylic acid sequence at the 5' end.

17. The chemically-modified siRNA according to claim 16, wherein the polydeoxyadenylic acid has a length of 40 bases, and phosphodiester bonds of the polydeoxyadenylic acid are phosphorothioated.

18. A schizophyllan/chemically-modified siRNA complex, wherein the chemically-modified siRNA according to claim 17 is complexed with schizophyllan.

19. A chemically-modified siRNA, comprising a sense strand and an antisense strand having the sequences:
Sense strand:
5'-C(F)AGA(M)AAC(F)A(M)GUUC(F)A(M)CCUU(F) G(M)Adtdt-3' (SEQ ID NO: 44)
Antisense strand:
5'-UCAAGGU(F)G(M)AACU(F)G(M)UUUCU(F) Gdtdt-3' (SEQ ID NO: 45)
wherein, dt denotes a deoxythymidylic acid residue, U(F) denotes a uridylic acid residue where the 2' hydroxy group has been replaced with a fluoro group, G(M) denotes a guanylic acid residue where a methoxy group has been substituted for the 2' hydroxy group, C(F) denotes a cytidylic acid residue where the 2' hydroxy group has been replaced with a fluoro group, and A(M) denotes an adenylic acid residue where a methoxy group has been substituted for the 2' hydroxy group, and
wherein the sense strand has a polydeoxyadenylic acid sequence at the 5' end.

20. The chemically-modified siRNA according to claim 19, wherein the polydeoxyadenylic acid has a length of 40 bases, and phosphodiester bonds of the polydeoxyadenylic acid are phosphorothioated.

21. A schizophyllan/chemically-modified siRNA complex, wherein the chemically-modified siRNA according to claim 20 is complexed with schizophyllan.

22. A chemically-modified siRNA, comprising a sense strand and an antisense strand having the sequences:
Sense strand:
5'-C(F)A(M)GGAGACCU(F)G(M)GC(F)A(M)CU(F)G (M)GAdtdt-3'(SEQ ID NO: 46)
Antisense strand:
5'-UCCAGUGCC(F)A(M)GGUCUCCU(F)Gdtdt-3' (SEQ ID NO: 47)
wherein, dt denotes a deoxythymidylic acid residue, U(F) denotes a uridylic acid residue where the 2' hydroxy group has been replaced with a fluoro group, G(M) denotes a guanylic acid residue where a methoxy group has been substituted for the 2' hydroxy group, C(F) denotes a cytidylic acid residue where the 2' hydroxy group has been replaced with a fluoro group, and A(M) denotes an adenylic acid residue where a methoxy group has been substituted for the 2' hydroxy group, and
wherein the sense strand has a polydeoxyadenylic acid sequence at the 5' end.

23. The chemically-modified siRNA according to claim 22, wherein the polydeoxyadenylic acid has a length of 40 bases, and phosphodiester bonds of the polydeoxyadenylic acid are phosphorothioated.

24. A schizophyllan/chemically-modified siRNA complex, wherein the chemically-modified siRNA according to claim 23 is complexed with schizophyllan.

\* \* \* \* \*

SEQUENCE LISTING

<160> NUMBER OF SEQ ID NOS: 47

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Sense strand of siRNA for CD40

<400> SEQUENCE: 1
cgugcaguga caaacaguat t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Antisense strand of siRNA for CD40

<400> SEQUENCE: 2
uacuguuugu cacugcacgt t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Sense strand of hsiCD40(208)

<400> SEQUENCE: 3
gacagaaacu ggugagugat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Antisense strand of hsiCD40(208)

<400> SEQUENCE: 4
ucacucacca guuucuguct t                                              21

<210> SEQ ID NO 5
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Sense strand of hsiCD40(867)

<400> SEQUENCE: 5
aguguggcca cgugggcaat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Antisense strand of hsiCD40(867)

<400> SEQUENCE: 6
uugcccacgu ggccacacut t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Sense strand of hsiCD40(1019)

<400> SEQUENCE: 7
cagaaacagu ucaccuugat t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Antisense strand of hsiCD40(1019)

<400> SEQUENCE: 8
ucaaggugaa cuguuucugt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

<223> OTHER INFORMATION: Sense strand of hsiCD40(998)

<400> SEQUENCE: 9
caggagaccu ggcacuggat t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Antisense strand of hsiCD40(998)

<400> SEQUENCE: 10
uccagugcca ggucuccugt t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 1

<400> SEQUENCE: 11
cgugcaguga caaacaguat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 1
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' methoxy modified nucleotide

```
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (15)..(15)
<223> OTHER INFORMATION: 2' fluoro modified nucleotide
<220> FEATURE:
<221> NAME/KEY: modified_base
<222> LOCATION: (16)..(16)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 12
cgugcaguga caaacaguat t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 2

<400> SEQUENCE: 13
uacuguuugu cacugcacgt t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 2
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' methoxy modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (14)..(14)
```

<223> OTHER INFORMATION: 2' fluoro modified nucleotide
<220> FEATURE:
<221> NAME/KEY: modified_base
<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' methoxy modified nucleotide

<400> SEQUENCE: 14
uacuguuugu cacugcacgt t                                            21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 1
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (2)..(2)
<223> OTHER INFORMATION: 2' methoxy modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' methoxy modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' methoxy modified nucleotide
<220> FEATURE:
<221> NAME/KEY: modified_base
<222> LOCATION: (10)..(10)
<223> OTHER INFORMATION: 2' methoxy modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide

```
<220> FEATURE:
<221> NAME/KEY: modified_base
<222> LOCATION: (13)..(13)
<223> OTHER INFORMATION: 2' methoxy modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
<221> NAME/KEY: modified_base
<222> LOCATION: (15)..(15)
<223> OTHER INFORMATION: 2' fluoro modified nucleotide
<220> FEATURE:
<221> NAME/KEY: modified_base
<222> LOCATION: (16)..(16)
<223> OTHER INFORMATION: 2' methoxy modified nucleotide
<220> FEATURE:
<221> NAME/KEY: modified_base
<222> LOCATION: (17)..(17)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 15
cgugcaguga caaacaguat t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 2
<220> FEATURE:
<221> NAME/KEY: modified_base
<222> LOCATION: (6)..(6)
<223> OTHER INFORMATION: 2' fluoro modified nucleotide
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' methoxy modified nucleotide
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (13)..(13)
<223> OTHER INFORMATION: 2' fluoro modified nucleotide
<220> FEATURE:
```

```
<221> NAME/KEY: modified_base
<222> LOCATION: (14)..(14)
<223> OTHER INFORMATION: 2' fluoro modified nucleotide
<220> FEATURE:
<221> NAME/KEY: modified_base
<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 16
uacuguuugu cacugcacgt t                                           21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 2
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (2)..(2)
<223> OTHER INFORMATION: 2' methoxy modified nucleotide
<220> FEATURE:
<221> NAME/KEY: modified_base
<222> LOCATION: (4)..(4)
<223> OTHER INFORMATION: 2' fluoro modified nucleotide
<220> FEATURE:
<221> NAME/KEY: modified_base
<222> LOCATION: (5)..(5)
<223> OTHER INFORMATION: 2' methoxy modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' methoxy modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (14)..(14)
<223> OTHER INFORMATION: 2' fluoro modified nucleotide
<220> FEATURE:
<221> NAME/KEY: modified_base
```

<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' methoxy modified nucleotide

<400> SEQUENCE: 17
uacuguuugu cacugcacgt t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 1
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (2)..(2)
<223> OTHER INFORMATION: 2' fluoro modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' fluoro modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' fluoro modified nucleotide
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (13)..(13)

```
<223> OTHER INFORMATION: 2' fluoro modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
<221> NAME/KEY: modified_base
<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' fluoro modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 18
cgugcaguga caaacaguat t                                           21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 1
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' methoxy modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
```

```
<220> FEATURE:
<221> NAME/KEY: modified_base
<222> LOCATION: (15)..(15)
<223> OTHER INFORMATION: 2' fluoro modified nucleotide
<220> FEATURE:
<221> NAME/KEY: modified_base
<222> LOCATION: (16)..(16)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 19
cgugcaguga caaacaguat t                                               21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand of siRNA for CD40
<220> FEATURE:
<221> NAME/KEY: modified_base
<222> LOCATION: (1)..(1)
<223> OTHER INFORMATION: 2' methoxy modified nucleotide

<400> SEQUENCE: 20
cggugaaagc gaauccuau u                                                21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand of siRNA for CD40

<400> SEQUENCE: 21
uaggaauucg cuuucaccgu u                                               21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 20
<220> FEATURE:
<221> NAME/KEY: modified_base
<222> LOCATION: (1)..(1)
<223> OTHER INFORMATION: 2' methoxy modified nucleotide

<400> SEQUENCE: 22
cggugaaagc gaauuccutt                                                 20

<210> SEQ ID NO 23
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 21

<400> SEQUENCE: 23
uaggaauucg cuuucaccgt t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 20
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' fluoro modified nucleotide
<220> FEATURE:
<221> NAME/KEY: modified_base
<222> LOCATION: (5)..(5)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 24
cggugaaagc gaauuccuat t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 21
<220> FEATURE:
<221> NAME/KEY: modified_base
<222> LOCATION: (15)..(15)
<223> OTHER INFORMATION: 2' fluoro modified nucleotide
<220> FEATURE:
<221> NAME/KEY: modified_base
<222> LOCATION: (16)..(16)
<223> OTHER INFORMATION: 2' methoxy modified nucleotide

<400> SEQUENCE: 25
uaggaauucg cuuucaccgt t                                              21
```

```
<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Sense strand of siRNA for CD40
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (2)..(2)
<223> OTHER INFORMATION: 2' methoxy modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (15)..(15)
<223> OTHER INFORMATION: 2' fluoro modified nucleotide
<220> FEATURE:
<221> NAME/KEY: modified_base
<222> LOCATION: (16)..(16)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 26
caugcagaga aaacaguat t                                                   21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Antisense strand of siRNA for CD40
<220> FEATURE:
<221> NAME/KEY: modified_base
<222> LOCATION: (14)..(14)
<223> OTHER INFORMATION: 2' fluoro modified nucleotide
<220> FEATURE:
<221> NAME/KEY: modified_base
<222> LOCATION: (15)..(15)
```

```
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide

<400> SEQUENCE: 27
uacuguuuuu cucugcaugt t                                              21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand of siRNA for CD40

<400> SEQUENCE: 28
ggagggcacc gcagaaucau u                                              21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand of siRNA for CD40

<400> SEQUENCE: 29
ugauucugcg gugcccuccu u                                              21

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 28
<220> FEATURE:
<221> NAME/KEY: modified_base
<222> LOCATION: (1)..(1)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' methoxy modified nucleotide
<220> FEATURE:
<221> NAME/KEY: modified_base
<222> LOCATION: (12)..(12)
<223> OTHER INFORMATION: 2' fluoro modified nucleotide
<220> FEATURE:
<221> NAME/KEY: modified_base
```

```
<222> LOCATION: (13)..(13)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 30
ggagggcacc gcagaaucau utt                                            23

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 29
<220> FEATURE:
<221> NAME/KEY: modified_base
<222> LOCATION: (8)..(8)
<223> OTHER INFORMATION: 2' methoxy modified nucleotide
<220> FEATURE:
<221> NAME/KEY: modified_base
<222> LOCATION: (12)..(12)
<223> OTHER INFORMATION: 2' fluoro modified nucleotide
<220> FEATURE:
<221> NAME/KEY: modified_base
<222> LOCATION: (13)..(13)
<223> OTHER INFORMATION: 2' methoxy modified nucleotide

<400> SEQUENCE: 31
ugauucugcg gugcccucct t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 3
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (2)..(2)
<223> OTHER INFORMATION: 2' fluoro modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' fluoro modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
```

<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' fluoro modified nucleotide
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (13)..(13)
<223> OTHER INFORMATION: 2' fluoro modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
<221> NAME/KEY: modified_base
<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' fluoro modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 32
gacagaaacu ggugagugat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 4
<220> FEATURE:
<221> NAME/KEY: modified_base
<222> LOCATION: (9)..(9)
<223> OTHER INFORMATION: 2' fluoro modified nucleotide
<220> FEATURE:
<221> NAME/KEY: modified_base

```
<222> LOCATION: (10)..(10)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' methoxy modified nucleotide

<400> SEQUENCE: 33
ucacucacca guuucuguct t                                         21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 3
<220> FEATURE:
<221> NAME/KEY: modified_base
<222> LOCATION: (1)..(1)
<223> OTHER INFORMATION: 2' methoxy modified nucleotide
<220> FEATURE:
<221> NAME/KEY: modified_base
<222> LOCATION: (2)..(2)
<223> OTHER INFORMATION: 2' methoxy modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (5)..(5)
<223> OTHER INFORMATION: 2' methoxy modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' methoxy modified nucleotide
<220> FEATURE:
<221> NAME/KEY: modified_base
<222> LOCATION: (8)..(8)
<223> OTHER INFORMATION: 2' methoxy modified nucleotide
<220> FEATURE:
<221> NAME/KEY: modified_base
<222> LOCATION: (9)..(9)
<223> OTHER INFORMATION: 2' fluoro modified nucleotide
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' methoxy modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (13)..(13)
```

```
<223> OTHER INFORMATION: 2' fluoro modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
<221> NAME/KEY: modified_base
<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' methoxy modified nucleotide
<220> FEATURE:
<221> NAME/KEY: modified_base
<222> LOCATION: (17)..(17)
<223> OTHER INFORMATION: 2' fluoro modified nucleotide
<220> FEATURE:
<221> NAME/KEY: modified_base
<222> LOCATION: (18)..(18)
<223> OTHER INFORMATION: 2' methoxy modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 34
gacagaaacu ggugagugat t                                      21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 3
<220> FEATURE:
<221> NAME/KEY: modified_base
<222> LOCATION: (1)..(1)
<223> OTHER INFORMATION: 2' methoxy modified nucleotide
<220> FEATURE:
<221> NAME/KEY: modified_base
<222> LOCATION: (2)..(2)
<223> OTHER INFORMATION: 2' methoxy modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' methoxy modified nucleotide
<220> FEATURE:
<221> NAME/KEY: modified_base
<222> LOCATION: (13)..(13)
<223> OTHER INFORMATION: 2' fluoro modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
<221> NAME/KEY: modified_base
<222> LOCATION: (17)..(17)
<223> OTHER INFORMATION: 2' fluoro modified nucleotide
```

```
<220> FEATURE:
<221> NAME/KEY: modified_base
<222> LOCATION: (18)..(18)
<223> OTHER INFORMATION: 2' methoxy modified nucleotide

<400> SEQUENCE: 35
gacagaaacu ggugagugat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 5
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (2)..(2)
<223> OTHER INFORMATION: 2' fluoro modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' fluoro modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' fluoro modified nucleotide
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (13)..(13)
<223> OTHER INFORMATION: 2' fluoro modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
```

```
<221> NAME/KEY: modified_base
<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' fluoro modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 36
aguguggcca cgugggcaat t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 6
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' methoxy modified nucleotide
<220> FEATURE:
<221> NAME/KEY: modified_base
<222> LOCATION: (14)..(14)
<223> OTHER INFORMATION: 2' fluoro modified nucleotide
<220> FEATURE:
<221> NAME/KEY: modified_base
<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' methoxy modified nucleotide

<400> SEQUENCE: 37
uugcccacgu ggccacacut t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 5
```

```
<220> FEATURE:
<221> NAME/KEY: modified_base
<222> LOCATION: (1)..(1)
<223> OTHER INFORMATION: 2' methoxy modified nucleotide
<220> FEATURE:
<221> NAME/KEY: modified_base
<222> LOCATION: (2)..(2)
<223> OTHER INFORMATION: 2' methoxy modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' methoxy modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' fluoro modified nucleotide
<220> FEATURE:
<221> NAME/KEY: modified_base
<222> LOCATION: (10)..(10)
<223> OTHER INFORMATION: 2' methoxy modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (13)..(13)
<223> OTHER INFORMATION: 2' fluoro modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
<221> NAME/KEY: modified_base
<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' methoxy modified nucleotide
<220> FEATURE:
<221> NAME/KEY: modified_base
<222> LOCATION: (17)..(17)
<223> OTHER INFORMATION: 2' fluoro modified nucleotide
<220> FEATURE:
<221> NAME/KEY: modified_base
<222> LOCATION: (18)..(18)
<223> OTHER INFORMATION: 2' methoxy modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 38
```
aguguggcca cgugggcaat t                                               21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 5
<220> FEATURE:
<221> NAME/KEY: modified_base
<222> LOCATION: (1)..(1)
<223> OTHER INFORMATION: 2' methoxy modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (9)..(9)
<223> OTHER INFORMATION: 2' fluoro modified nucleotide
<220> FEATURE:
<221> NAME/KEY: modified_base
<222> LOCATION: (10)..(10)
<223> OTHER INFORMATION: 2' methoxy modified nucleotide
<220> FEATURE:
<221> NAME/KEY: modified_base
<222> LOCATION: (13)..(13)
<223> OTHER INFORMATION: 2' fluoro modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
<221> NAME/KEY: modified_base
<222> LOCATION: (17)..(17)
<223> OTHER INFORMATION: 2' fluoro modified nucleotide
<220> FEATURE:
<221> NAME/KEY: modified_base
<222> LOCATION: (18)..(18)
<223> OTHER INFORMATION: 2' methoxy modified nucleotide

<400> SEQUENCE: 39
aguguggcca cgugggcaat t                                               21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 7
<220> FEATURE:
<221> NAME/KEY: modified_base

```
<222> LOCATION: (1)..(1)
<223> OTHER INFORMATION: 2' fluoro modified nucleotide
<220> FEATURE:
<221> NAME/KEY: modified_base
<222> LOCATION: (2)..(2)
<223> OTHER INFORMATION: 2' fluoro modified nucleotide
<220> FEATURE:
<221> NAME/KEY: modified_base
<222> LOCATION: (3)..(3)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' fluoro modified nucleotide
<220> FEATURE:
<221> NAME/KEY: modified_base
<222> LOCATION: (5)..(5)
<223> OTHER INFORMATION: 2' fluoro modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' fluoro modified nucleotide
<220> FEATURE:
<221> NAME/KEY: modified_base
<222> LOCATION: (9)..(9)
<223> OTHER INFORMATION: 2' fluoro modified nucleotide
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' methoxy modified nucleotide
<220> FEATURE:
<221> NAME/KEY: modified_base
<222> LOCATION: (13)..(13)
<223> OTHER INFORMATION: 2' fluoro modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
<221> NAME/KEY: modified_base
<222> LOCATION: (15)..(15)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' fluoro modified nucleotide
<220> FEATURE:
<221> NAME/KEY: modified_base
<222> LOCATION: (18)..(18)
<223> OTHER INFORMATION: 2' fluoro modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 40
cagaaacagu ucaccuugat t                                    21
```

```
<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 8
<220> FEATURE:
<221> NAME/KEY: modified_base
<222> LOCATION: (12)..(12)
<223> OTHER INFORMATION: 2' fluoro modified nucleotide
<220> FEATURE:
<221> NAME/KEY: modified_base
<222> LOCATION: (13)..(13)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide

<400> SEQUENCE: 41
ucaaggugaa cuguuucugt t                                           21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 7
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (2)..(2)
<223> OTHER INFORMATION: 2' methoxy modified nucleotide
<220> FEATURE:
<221> NAME/KEY: modified_base
<222> LOCATION: (3)..(3)
<223> OTHER INFORMATION: 2' methoxy modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (5)..(5)
<223> OTHER INFORMATION: 2' methoxy modified nucleotide
<220> FEATURE:
<221> NAME/KEY: modified_base
<222> LOCATION: (6)..(6)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' methoxy modified nucleotide
<220> FEATURE:
<221> NAME/KEY: modified_base
<222> LOCATION: (9)..(9)
<223> OTHER INFORMATION: 2' methoxy modified nucleotide
```

```
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' fluoro modified nucleotide
<220> FEATURE:
<221> NAME/KEY: modified_base
<222> LOCATION: (12)..(12)
<223> OTHER INFORMATION: 2' fluoro modified nucleotide
<220> FEATURE:
<221> NAME/KEY: modified_base
<222> LOCATION: (13)..(13)
<223> OTHER INFORMATION: 2' methoxy modified nucleotide
<220> FEATURE:
<221> NAME/KEY: modified_base
<222> LOCATION: (14)..(14)
<223> OTHER INFORMATION: 2' fluoro modified nucleotide
<220> FEATURE:
<221> NAME/KEY: modified_base
<222> LOCATION: (15)..(15)
<223> OTHER INFORMATION: 2' fluoro modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' fluoro modified nucleotide
<220> FEATURE:
<221> NAME/KEY: modified_base
<222> LOCATION: (18)..(18)
<223> OTHER INFORMATION: 2' methoxy modified nucleotide
<220> FEATURE:
<221> NAME/KEY: modified_base
<222> LOCATION: (19)..(19)
<223> OTHER INFORMATION: 2' methoxy modified nucleotide

<400> SEQUENCE: 42
cagaaacagu ucaccuugat t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 8
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' methoxy modified nucleotide
<220> FEATURE:
<221> NAME/KEY: modified_base
<222> LOCATION: (12)..(12)
<223> OTHER INFORMATION: 2' fluoro modified nucleotide
<220> FEATURE:
<221> NAME/KEY: modified_base
<222> LOCATION: (13)..(13)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide
```

-continued

```
<400> SEQUENCE: 43
ucaaggugaa cuguuucugt t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 7
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (4)..(4)
<223> OTHER INFORMATION: 2' methoxy modified nucleotide
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' methoxy modified nucleotide
<220> FEATURE:
<221> NAME/KEY: modified_base
<222> LOCATION: (12)..(12)
<223> OTHER INFORMATION: 2' fluoro modified nucleotide
<220> FEATURE:
<221> NAME/KEY: modified_base
<222> LOCATION: (13)..(13)
<223> OTHER INFORMATION: 2' methoxy modified nucleotide
<220> FEATURE:
<221> NAME/KEY: modified_base
<222> LOCATION: (17)..(17)
<223> OTHER INFORMATION: 2' fluoro modified nucleotide
<220> FEATURE:
<221> NAME/KEY: modified_base
<222> LOCATION: (18)..(18)
<223> OTHER INFORMATION: 2' methoxy modified nucleotide

<400> SEQUENCE: 44
cagaaacagu ucaccuugat t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 8
<220> FEATURE:
<221> NAME/KEY: modified_base
<222> LOCATION: (7)..(7)
<223> OTHER INFORMATION: 2' fluoro modified nucleotide
<220> FEATURE:
<221> NAME/KEY: modified_base
<222> LOCATION: (8)..(8)
<223> OTHER INFORMATION: 2' methoxy modified nucleotide
<220> FEATURE:
<221> NAME/KEY: modified_base
<222> LOCATION: (12)..(12)
<223> OTHER INFORMATION: 2' fluoro modified nucleotide
```

```
<220> FEATURE:
<221> NAME/KEY: modified_base
<222> LOCATION: (13)..(13)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide

<400> SEQUENCE: 45
ucaaggugaa cuguuucugt t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 9
<220> FEATURE:
<221> NAME/KEY: modified_base
<222> LOCATION: (1)..(1)
<223> OTHER INFORMATION: 2' fluoro modified nucleotide
<220> FEATURE:
<221> NAME/KEY: modified_base
<222> LOCATION: (2)..(2)
<223> OTHER INFORMATION: 2' methoxy modified nucleotide
<220> FEATURE:
<221> NAME/KEY: modified_base
<222> LOCATION: (10)..(10)
<223> OTHER INFORMATION: 2' fluoro modified nucleotide
<220> FEATURE:
<221> NAME/KEY: modified_base
<222> LOCATION: (11)..(11)
<223> OTHER INFORMATION: 2' methoxy modified nucleotide
<220> FEATURE:
<221> NAME/KEY: modified_base
<222> LOCATION: (13)..(13)
<223> OTHER INFORMATION: 2' fluoro modified nucleotide
<220> FEATURE:
<221> NAME/KEY: modified_base
<222> LOCATION: (14)..(14)
<223> OTHER INFORMATION: 2' methoxy modified nucleotide
<220> FEATURE:
<221> NAME/KEY: modified_base
<222> LOCATION: (16)..(16)
<223> OTHER INFORMATION: 2' fluoro modified nucleotide
<220> FEATURE:
<221> NAME/KEY: modified_base
<222> LOCATION: (17)..(17)
<223> OTHER INFORMATION: 2' methoxy modified nucleotide

<400> SEQUENCE: 46
caggagaccu ggcacuggat t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Modified SEQ ID NO: 10
<220> FEATURE:
<221> NAME/KEY: modified_base
<222> LOCATION: (9)..(9)
```

<223> OTHER INFORMATION: 2' fluoro modified nucleotide
<220> FEATURE:
<221> NAME/KEY: modified_base
<222> LOCATION: (10)..(10)
<223> OTHER INFORMATION: 2' methoxy modified nucleotide
<220> FEATURE:
<221> NAME/KEY: modified_base
<222> LOCATION: (18)..(18)
<223> OTHER INFORMATION: 2' fluoro modified nucleotide

<400> SEQUENCE: 47
uccagugcca ggucuccugt t                                          21